(12) United States Patent
Wadehra et al.

(10) Patent No.: US 11,053,310 B2
(45) Date of Patent: Jul. 6, 2021

(54) ANTIBODIES FOR THE TREATMENT OF CANCERS

(71) Applicant: THE REGENTS OF THE UNIVERSITY OF CALIFORNIA, Oakland, CA (US)

(72) Inventors: Madhuri Wadehra, Fontana, CA (US); Jonathan Braun, Tarzana, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 141 days.

(21) Appl. No.: 15/780,334

(22) PCT Filed: Dec. 5, 2016

(86) PCT No.: PCT/US2016/065002
§ 371 (c)(1),
(2) Date: May 31, 2018

(87) PCT Pub. No.: WO2017/096397
PCT Pub. Date: Jun. 8, 2017

(65) Prior Publication Data
US 2019/0040127 A1    Feb. 7, 2019

Related U.S. Application Data

(60) Provisional application No. 62/263,561, filed on Dec. 4, 2015.

(51) Int. Cl.
| | | |
|---|---|---|
| *C07K 16/30* | (2006.01) | |
| *A61K 39/00* | (2006.01) | |
| *C07K 16/28* | (2006.01) | |
| *A61K 47/68* | (2017.01) | |
| *G01N 33/574* | (2006.01) | |
| *G01N 33/577* | (2006.01) | |
| *A61P 35/00* | (2006.01) | |
| *C07K 16/22* | (2006.01) | |

(52) U.S. Cl.
CPC .......... *C07K 16/28* (2013.01); *A61K 47/6803* (2017.08); *A61K 47/6849* (2017.08); *A61K 47/6851* (2017.08); *A61P 35/00* (2018.01); *C07K 16/22* (2013.01); *C07K 16/2863* (2013.01); *C07K 16/30* (2013.01); *G01N 33/574* (2013.01); *G01N 33/577* (2013.01); *G01N 33/57492* (2013.01); *A61K 2039/505* (2013.01); *C07K 2317/40* (2013.01); *C07K 2317/565* (2013.01); *C07K 2317/73* (2013.01); *C07K 2317/92* (2013.01); *C07K 2317/94* (2013.01); *G01N 2333/705* (2013.01)

(58) Field of Classification Search
CPC .... C07K 16/28; C07K 16/22; C07K 16/2863; A61P 35/00; G01N 33/57492; A61K 47/6849; A61K 2039/505
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis |
| 4,301,144 A | 11/1981 | Iwashita et al. |
| 4,496,689 A | 1/1985 | Mitra et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 4,975,278 A | 12/1990 | Senter et al. |
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,821,337 A | 10/1998 | Carter et al. |
| 5,859,205 A | 1/1999 | Adair et al. |
| 6,054,297 A | 4/2000 | Carter et al. |
| 6,180,370 B1 | 1/2001 | Queen et al. |
| 6,407,213 B1 | 6/2002 | Carter et al. |
| 6,949,245 B1 | 9/2005 | Sliwkowski |

(Continued)

FOREIGN PATENT DOCUMENTS

| | | |
|---|---|---|
| WO | WO 1988/007378 | 10/1988 |
| WO | WO 1992/011018 | 7/1992 |

(Continued)

OTHER PUBLICATIONS

Abad, Morales et al., Invest Opthalmol Vis Sci (2008).
Abrami et al., J Biol Chem 276:30729-36 (2001).
Amersdorfer et al., Vaccine. 20:11-12 pp. 1640-1658 (2002).
Baca et al., J. Biol. Chem. 272(16):10678-10684 (1997).
Bird et al., Science 242:423-426 (1998).
Carter et al., Proc Natl Acad Sci USA 89:4285-9 (1992).
Claas et al., J Biol Chem 276:7974-84 (2001).
De Pascalis et al., J. Immunol. 169:3076-3084 (2002).
Duksin et al., J. Biol. Chem. 257:3105 (1982).
Edge et al., Anal. Biochem. 118:131 (1981).
Fu et al., Molecular Cancer Therapeutics. 13:4, pp. 902-915 (2014).
Galbiati et al., Cell 106:403-11 (2001).
Gorman et al., Proc. Natl. Acad. Sci. USA 88:4181-4185 (1991).
Gruenberg et al., Curr Opin Cell Biol 7: 552-63 (1995).
Hasse et al., J Neurosci Res 69:227-32 (2002).

(Continued)

*Primary Examiner* — Lei Yao
(74) *Attorney, Agent, or Firm* — Morgan, Lewis & Bockius LLP; Jeffry S. Mann; Louis T. Nguyen

(57) ABSTRACT

Provided herein are novel anti-EMP2 antibodies useful for the treatment and diagnosis of cancers that express or overexpress EMP2. In one aspect, provided herein is an isolated antibody that binds to Epithelial Membrane Protein 2 (EMP2), that includes heavy chain variable region and a light chain variable region. The heavy chain variable region includes three heavy chain complementary determining regions (HCDRs) and the light chain variable region includes three light chain variable regions (LCDRs). In some embodiments, the sequence of HCDR1 is SEQ ID NO: 11, the sequence of HCDR2 is SEQ ID NO: 12, the sequence of HCDR3 is SEQ ID NO: 13, the sequence of LCDR1 is SEQ ID NO:14, the sequence of LCDR2 is SEQ ID NO: 15, and the sequence of LCDR3 is SEQ ID NO: 16.

8 Claims, 16 Drawing Sheets

Specification includes a Sequence Listing.

(56) References Cited

U.S. PATENT DOCUMENTS

| | | |
|---|---|---|
| 7,657,380 B2 | 2/2010 | Lazar et al. |
| 2001/0035606 A1 | 11/2001 | Schoen |
| 2010/0272732 A1 | 10/2010 | Braun et al. |
| 2013/0004493 A1* | 1/2013 | Gordon .................. C07K 16/28 424/135.1 |
| 2013/0323249 A1 | 12/2013 | Zhou et al. |

FOREIGN PATENT DOCUMENTS

| | | |
|---|---|---|
| WO | WO 1994/013804 | 6/1994 |
| WO | WO 2003/011161 | 2/2003 |
| WO | WO 2003/057881 | 7/2003 |
| WO | WO 2006/094014 | 9/2006 |
| WO | WO 2011/039370 | 4/2011 |
| WO | WO 2011/053759 | 5/2011 |
| WO | WO 2013/056248 | 4/2013 |
| WO | WO 2013/148263 | 10/2013 |

OTHER PUBLICATIONS

He et al., J. Immunol. 160: 1029-1035 (1998).
Hecht et al., J Clin Oncol 24:4783-91 (2006).
Holliger et al.,Proc. Natl. Acad. Sci. U.S.A. 90:6444-6448 (1993).
Huston et al., Proc. Natl. Acad. Sci. U.S.A. 85:5879-5883 (1988).
Jones, Nature 321:522-525 (1986).
Krauss et al., Protein Engineering 16(10):753-759 (2003).
Leitinger et al., J Cell Sci 115:963-72 (2002).
Moffett et al., J Biol Chem 275:2191-8 (2000).
O'Connor et al., Protein Eng 11:321-8 (1998).
Perera et al., Transfusion. 40:7 (2000).
Presta et al., Cancer Res. 57(20):4593-9 (1997).
Queen et al., Proc Natl Acad Sci, USA 86:10029-33 (1989).
Rader et al., Proc. Natl. Acad. Sci. USA 95: 8910-8915 (1998).
Riechmann et al., Nature 332:323-329 (1988).
Roguska et al., Proc. Natl. Acad. Sci. USA 91:969-973 (1994).
Roque et al., Biotechnol. Prog. 20:639-654 (2004).
Rosok et al., J. Biol. Chem. 271(37): 22611-22618 (1996).
Sherman, Mod Pathol 13:295-308 (2000).
Sojar and Bahl., Arch. Biochem. Biophys. 259:52 (1987).
Sun et al., Nature Communications. 6:8322 (Genbank supplement) (2015).
Tan et al., J. Immunol. 169:1119-1125 (2002).
Thotakura et al., Meth. Enzymol. 138:350 (1987).
Tomlinson et. al., Methods Enzymol. 326:461-479 (2000).
Verhoeyen et al., Science 239:1534-1536 (1988).
Wadehra et al., J Biol Chem 277:41094-41100 (2002).
Wadehra et al., Exp Mol Pathol 74:106-12 (2003).
Wadehra et al., Clin Immunol 107:129-136 (2003).
Wadehra et al., Mol Biol Cell 15:2073-2083 (2004).
Wadehra et al., Dev Biol 287:336-45 (2005).
Wadehra et al., Cancer 107:90-8 (2006).
Wadehra et al., Cancer Research. Abstract 665 (2014).
Wadehra et al., Cancer Research. Abstract 654. (2015).
Wadehra et al., Journal of Clinical Oncology. (2014).
Wu et al., J. Mol. Biol. 294:151-162 (1999).
Caldas et al., Molecular Immunology, vol. 39, pp. 941-952 (2003).
Du et al., J. Mol. Biol., vol. 382, pp. 835-842 (2008).

* cited by examiner

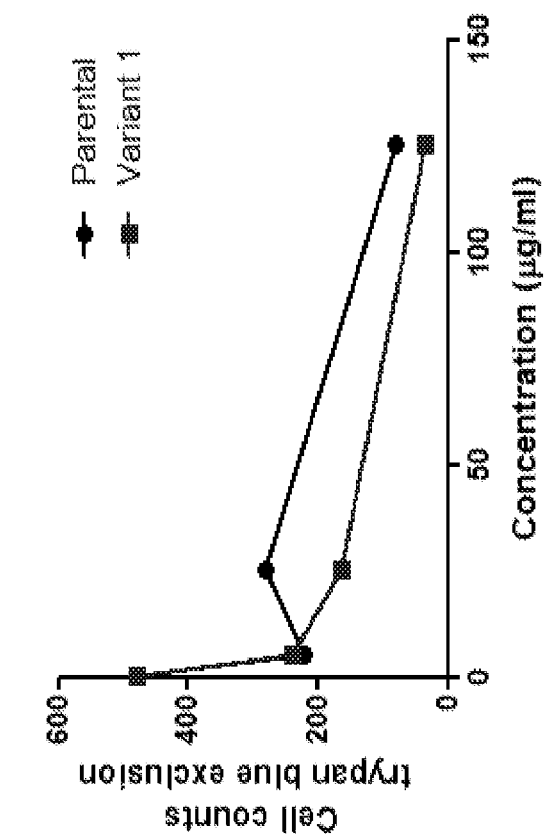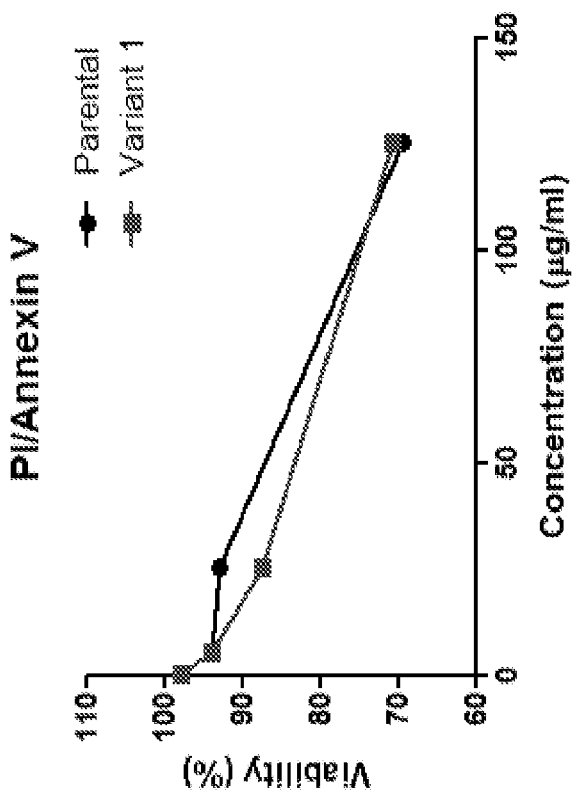
Figure 5

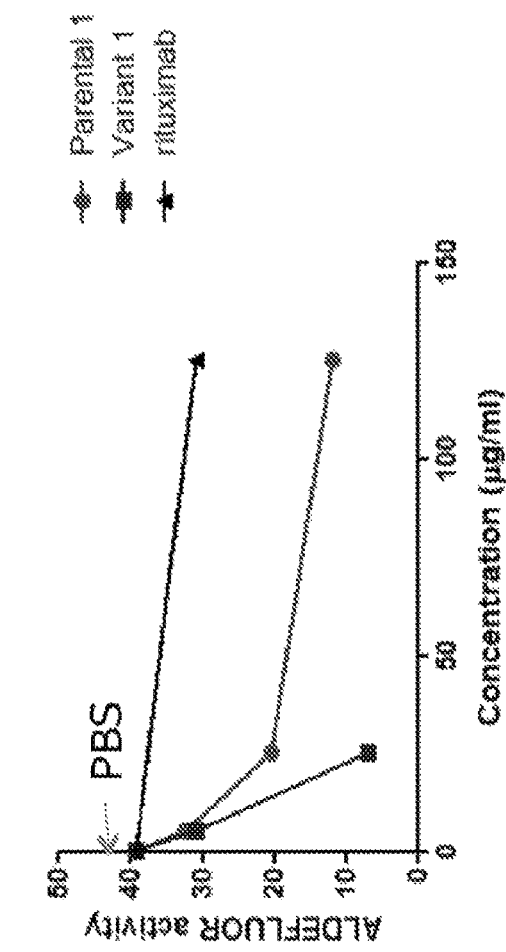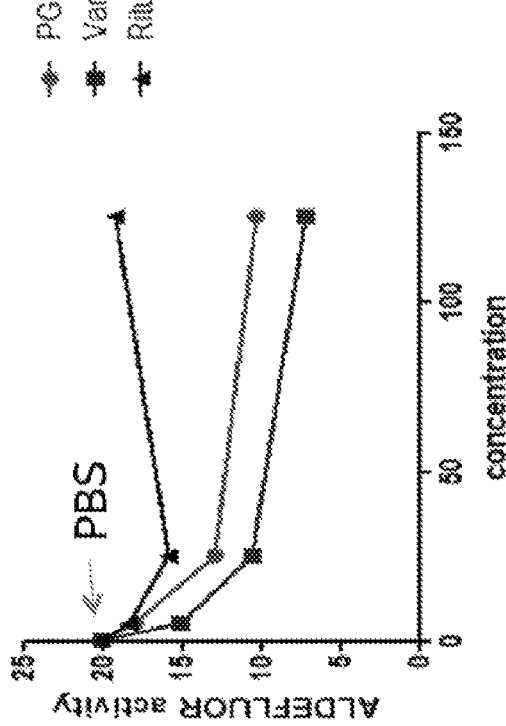
Figure 8

PG101: SEQUENCE TO ANALYZE

<---CDR3---
LQDYNGWT
↑

| Query | Observed | Mr (expt) | Mr (calc) | ppm | Miss | Score | Expect | Rank | Unique | Peptide |
|---|---|---|---|---|---|---|---|---|---|---|
| 1217 | 736.8328 | 1471.6510 | 1471.6368 | 9.65 | 0 | (46) | | | | Q.DYNGWT FGQGTKV.D U + [-0.0364 at K12] |
| | | | | | | | | 1 | | Q.DYNGWT FGQGTKV.D |
| 1218 | 736.8433 | 1471.6720 | 1471.6732 | -0.80 | 0 | (47) | 9.4e-005 | 1 | U | Q.DYNGWTFGQGTKV.D |
| 1219 | 491.5648 | 1471.6726 | 1471.6732 | -0.43 | 0 | (22) | | 1 | U | Q.DYNGWTFGQGTKV.D + Deamidated (NQ); [-0.9840 at C-term V] |
| 1220 | 491.5654 | 1471.6744 | 1471.6732 | 0.79 | 0 | (21) | | 1 | U | Q.DYNGWTFGQGTKV.D + Deamidated (NQ); [-0.9840 at C-term V] |
| 1221 | 737.3201 | 1472.6256 | 1472.6209 | 3.26 | 0 | (36) | | 1 | U | Q.DYNGWTFGQGTKV.D + Deamidated (NQ); [-0.0364 at K12] |
| 1222 | 737.3209 | 1472.6272 | 1472.6209 | 4.34 | 0 | (31) | | 1 | U | Q.DYNGWTFGQGTKV.D + Deamidated (NQ); [-0.0364 at K12] |
| 1223 | 737.3214 | 1472.6282 | 1472.6209 | 5.02 | 0 | (31) | | 1 | U | Q.DYNGWTFGQGTKV.D + Deamidated (NQ); [-0.0364 at K12] |
| 1224 | 737.3221 | 1472.6296 | 1472.6209 | 5.97 | 0 | (30) | | 1 | U | Q.DYNGWTFGQGTKV.D + Deamidated (NQ); [-0.0364 at K12] |
| 1225 | 737.3224 | 1472.6302 | 1472.6209 | 6.38 | 0 | (35) | | 1 | U | Q.DYNGWTFGQGTKV.D + Deamidated (NQ); [-0.0364 at K12] |
| 1226 | 737.3342 | 1472.6538 | 1472.6572 | -2.30 | 0 | (26) | | 1 | U | Q.DYNGWTFGQGTKV.D + 2 Deamidated (NQ); [-0.9840 at N-term D] |
| 1227 | 737.3351 | 1472.6556 | 1472.6572 | -1.07 | 0 | (40) | 0.00046 | 1 | U | Q.DYNGWTFGQGTKV.D + Deamidated (NQ) |

Figure 13

SEQUENCE LISTING

<160> NUMBER OF SEQ ID NOS: 24

<210> SEQ ID NO 1
<211> LENGTH: 167
<212> TYPE: PRT
<213> ORGANISM: Homo sapiens

<400> SEQUENCE: 1

Met Leu Val Leu Leu Ala Phe Ile Ile Ala Phe His Ile Thr Ser Ala
1               5                   10                  15

Ala Leu Leu Phe Ile Ala Thr Val Asp Asn Ala Trp Trp Val Gly Asp
            20                  25                  30

Glu Phe Phe Ala Asp Val Trp Arg Ile Cys Thr Asn Asn Thr Asn Cys
        35                  40                  45

Thr Val Ile Asn Asp Ser Phe Gln Glu Tyr Ser Thr Leu Gln Ala Val
    50                  55                  60

Gln Ala Thr Met Ile Leu Ser Thr Ile Leu Cys Cys Ile Ala Phe Phe
65                  70                  75                  80

Ile Phe Val Leu Gln Leu Phe Arg Leu Lys Gln Gly Glu Arg Phe Val
                85                  90                  95

Leu Thr Ser Ile Ile Gln Leu Met Ser Cys Leu Cys Val Met Ile Ala
            100                 105                 110

Ala Ser Ile Tyr Thr Asp Arg Arg Glu Asp Ile His Asp Lys Asn Ala
        115                 120                 125

Lys Phe Tyr Pro Val Thr Arg Glu Gly Ser Tyr Gly Tyr Ser Tyr Ile
    130                 135                 140

Leu Ala Trp Val Ala Phe Ala Cys Thr Phe Ile Ser Gly Met Met Tyr
145                 150                 155                 160

Leu Ile Leu Arg Lys Arg Lys
                165

<210> SEQ ID NO 2
<211> LENGTH: 20
<212> TYPE: PRT
<213> ORGANISM: Homo sapiens

<400> SEQUENCE: 2

Glu Asp Ile His Asp Lys Asn Ala Lys Phe Tyr Pro Val Thr Arg Glu
1               5                   10                  15

Gly Ser Tyr Gly
            20

<210> SEQ ID NO 3
<211> LENGTH: 121
<212> TYPE: PRT
<213> ORGANISM: Artificial Sequence
<220> FEATURE:
<223> OTHER INFORMATION: PG-101 heavy chain variable region domain

<400> SEQUENCE: 3

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Gly Arg Lys Ser Ala Gly Ile Asp Tyr Trp Gly
            100                 105                 110

Gln Gly Thr Leu Val Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: PG-101 variant 1 light chain variable region
      domain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Ser Gly Trp Thr
                85                  90                  95

Phe Gly Gln Gly Thr Lys Val Asp Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: PG-101 Variant 2 light chain variable region
    domain

<400> SEQUENCE: 5

Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Leu Trp Thr
                85                  90                  95

Phe Gly Gln Gly Thr Lys Val Asp Ile Lys
            100                 105

<210> SEQ ID NO 6
<211> LENGTH: 450
<212> TYPE: PRT
<213> ORGANISM: Artificial Sequence
<220> FEATURE:
<223> OTHER INFORMATION: PG-101 heavy chain

<400> SEQUENCE: 6

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Gly Arg Lys Ser Ala Gly Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 7
<211> LENGTH: 213
<212> TYPE: PRT
<213> ORGANISM: Artificial Sequence
<220> FEATURE:
<223> OTHER INFORMATION: PG-101 variant 1 light chain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Ser Gly Trp Thr
                85                  90                  95

Phe Gly Gln Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 8
<211> LENGTH: 213
<212> TYPE: PRT
<213> ORGANISM: Artificial Sequence
<220> FEATURE:
<223> OTHER INFORMATION: PG-101 Variant 2 light chain

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Leu Trp Thr
                85                  90                  95

Phe Gly Gln Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210
```

<210> SEQ ID NO 9
<211> LENGTH: 106
<212> TYPE: PRT
<213> ORGANISM: Artificial Sequence
<220> FEATURE:
<223> OTHER INFORMATION: PG-101 parental light chain variable region
      domain

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Gly Trp Thr
                85                  90                  95

Phe Gly Gln Gly Thr Lys Val Asp Ile Lys
            100                 105
```

<210> SEQ ID NO 10
<211> LENGTH: 213
<212> TYPE: PRT
<213> ORGANISM: Artificial Sequence
<220> FEATURE:
<223> OTHER INFORMATION: PG-101 parental light chain

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Gly Trp Thr
                85                  90                  95

Phe Gly Gln Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 11
<211> LENGTH: 5
<212> TYPE: PRT

```
<213> ORGANISM: Artificial Sequence
<220> FEATURE:
<223> OTHER INFORMATION: Variable heavy chain CDR1

<400> SEQUENCE: 11

Ser Tyr Ala Met His
1               5

<210> SEQ ID NO 12
<211> LENGTH: 17
<212> TYPE: PRT
<213> ORGANISM: Artificial Sequence
<220> FEATURE:
<223> OTHER INFORMATION: [Variable heavy chain CDR2

<400> SEQUENCE: 12

Val Ile Ser Tyr Asp Gly Ser Asn Lys Tyr Tyr Ala Asp Ser Val Lys
1               5                   10                  15

Gly

<210> SEQ ID NO 13
<211> LENGTH: 12
<212> TYPE: PRT
<213> ORGANISM: Artificial Sequence
<220> FEATURE:
<223> OTHER INFORMATION: Variable heavy chain CDR3

<400> SEQUENCE: 13

Asp Arg Arg Gly Arg Lys Ser Ala Gly Ile Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Variable light chain CDR1

<400> SEQUENCE: 14

Gln Ala Ser Gln Asp Ile Ser Asn Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Variable light chain CDR2

<400> SEQUENCE: 15

Ala Ala Ser Ser Leu Gln Ser
1               5

<210> SEQ ID NO 16
<211> LENGTH: 8
<212> TYPE: PRT
<213> ORGANISM: Artificial Sequence
<220> FEATURE:
<223> OTHER INFORMATION: Variable light chain CDR3

<400> SEQUENCE: 16

Leu Gln Asp Tyr Ser Gly Trp Thr
1               5

<210> SEQ ID NO 17
<211> LENGTH: 474
```

<212> TYPE: PRT
<213> ORGANISM: Artificial Sequence
<220> FEATURE:
<223> OTHER INFORMATION: PG-101 Parental Heavy Chain-hIgG1 antibody

<400> SEQUENCE: 17

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Gly Gly Val Val Gln Pro Gly Arg Ser Leu Arg Leu Ser Cys Ala Ala
        35                  40                  45

Ser Gly Phe Thr Phe Ser Ser Tyr Ala Met His Trp Val Arg Gln Ala
    50                  55                  60

Pro Gly Lys Gly Leu Glu Trp Val Ala Val Ile Ser Tyr Asp Gly Ser
65                  70                  75                  80

Asn Lys Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Arg Asp Arg Arg Gly Arg Lys
        115                 120                 125

Ser Ala Gly Ile Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

```
Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly
465                 470

<210> SEQ ID NO 18
<211> LENGTH: 233
<212> TYPE: PRT
<213> ORGANISM: Artificial Sequence
<220> FEATURE:
<223> OTHER INFORMATION: PG-101 Parental Light Chain-hKappa antibody

<400> SEQUENCE: 18

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Asn Gly Trp Thr Phe Gly Gln Gly Thr Lys Val Asp Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 19
<211> LENGTH: 233
<212> TYPE: PRT
<213> ORGANISM: Artificial Sequence
<220> FEATURE:
```

<223> OTHER INFORMATION: PG-101 Light Chain Variant 1-hKappa antibody

<400> SEQUENCE: 19

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Ser Gly Trp Thr Phe Gly Gln Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 20
<211> LENGTH: 233
<212> TYPE: PRT
<213> ORGANISM: Artificial Sequence
<220> FEATURE:
<223> OTHER INFORMATION: PG-101 Light Chain Variant 2-hKappa antibody

<400> SEQUENCE: 20

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Asp Tyr
            100                 105                 110

Asn Leu Trp Thr Phe Gly Gln Gly Thr Lys Val Asp Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 21
<211> LENGTH: 1425
<212> TYPE: DNA
<213> ORGANISM: Artificial Sequence
<220> FEATURE:
<223> OTHER INFORMATION: PG-101 Parental Heavy Chain-hIgG1 nucleotide

<400> SEQUENCE: 21

```
atggacccca agggcagcct gagctggaga atcctgctgt tcctgagcct ggccttcgag    60
ctgagctacg ccaggtgca gctggtgcag tctggcggcg agtggtgca gcctggaaga    120 tccctgagac tgtcctgtgc cgcctccggc ttcaccttct ccagctacgc tatgcactgg    180
gtgcgacagg cccctggcaa gggactggaa tgggtggccg tgatctccta cgacggctcc    240
aacaagtact acgccgactc cgtgaagggc cggttcacca ctcccgggga caactccaag    300
aacaccctgt acctgcagat gaactccctg cgggccgagg acaccgccgt gtactactgc    360
gccagagaca gacggggcag aaagtccgcc ggcatcgatt attggggcca gggcaccctc    420
gtgaccgtgt cctctgctag caccaagggc cccagcgtgt tcctctggc cccagcagc    480 aagagcacca gcggcggaac cgccgccctg ggctgctgg tgaaggacta cttccccgag    540
cccgtgaccg tgtcctggaa cagcggcgct ctgaccagcg agtgcacac cttcctgcc    600 gtgctgcaga gcagcggcct gtactccctg agcagcgtgg tgaccgtgcc agcagcagc    660 ctgggcaccc agacctacat ctgcaacgtg aaccacaagc cctccaacac caaggtggac    720
aagaaggtgg agcctaagag ctgcgacaag acccacacct gccctccctg ccccgccccc    780
gagctgctgg gcgacccag cgtgttcctg ttccctccca gcccaagga caccctgatg    840 atcagccgca ccccgaggt gacctgcgtg gtggtggacg tgagccacga ggaccccgag    900
gtgaagttca actggtacgt ggacggcgtg gaggtgcaca acgccaagac caagcctcgg    960
gaggagcagt acaactccac ctaccgcgtg gtgagcgtgc tgaccgtgct gcaccaggac    1020
tggctgaacg gcaaggagta caagtgcaag gtgagcaaca aggccctgcc cgctcccatc    1080
gagaagacca tcagcaaggc caagggccag ccccgggagc ctcaggtgta caccctgccc    1140 ccagccgcg acgagctgac caagaaccag gtgagcctga cctgctggt gaagggcttc    1200 taccctccg acatcgccgt ggagtgggag agcaacggcc agcctgagaa caactacaag    1260 accaccctc ccgtgctgga cagcgacggc agcttcttcc tgtacagcaa gctgaccgtg    1320
```

```
gacaagtccc ggtggcagca gggcaacgtg ttcagctgca gcgtgatgca cgaggccctg    1380
cacaaccact acacccagaa gagcctgagc ctgagccccg atag                      1425

<210> SEQ ID NO 22
<211> LENGTH: 702
<212> TYPE: DNA
<213> ORGANISM: Artificial Sequence
<220> FEATURE:
<223> OTHER INFORMATION: PG-101 Parental Light Chain-hKappa nucleotide

<400> SEQUENCE: 22
atggagaccg acaccctgct gctctgggtg ctgctgctct gggtgcccgg ctccaccgga      60
gacatccaga tgacccagtc cccctccagc ctgtctgcct ctgtgggcga cagagtgacc     120
atcacctgtc aggcctccca ggacatctcc aactacctga actggtatca gcagaagccc     180
ggcaaggccc ccaagctgct gatctacgct gccagctctc tgcagtccgg cgtgccctct     240
agattctccg gctctggctc tggcaccgac tttaccctga ccatcagctc cctgcagccc     300
gaggacttcg ccacctacta ctgtctgcaa gactacaacg ctggaccttc ggccagggc     360 accaaggtgg acatcaagcg gaccgtggcc gcccccagcg tgttcatctt ccctcccagc     420
gacgagcagc tgaagtctgg caccgccagc gtggtgtgcc tgctgaacaa cttctacccc     480
cgcgaggcca aggtgcagtg gaaggtggac aacgccctgc agagcggcaa cagccaggag     540
agcgtgaccg agcaggactc caaggacagc acctacagcc tgagcagcac cctgaccctg     600
agcaaggccg actacgagaa gcacaaggtg tacgcctgcg aggtgaccca ccagggactg     660
tctagccccg tgaccaagag cttcaaccgg ggcgagtgct aa                         702

<210> SEQ ID NO 23
<211> LENGTH: 702
<212> TYPE: DNA
<213> ORGANISM: Artificial Sequence
<220> FEATURE:
<223> OTHER INFORMATION: PG-101 Light Chain Variant 1-hKappa nucleotide

<400> SEQUENCE: 23
atggagaccg acaccctgct gctctgggtg ctgctgctct gggtgcccgg ctccaccgga      60
gacatccaga tgacccagtc cccctccagc ctgtctgcct ctgtgggcga cagagtgacc     120
atcacctgtc aggcctccca ggacatctcc aactacctga actggtatca gcagaagccc     180
ggcaaggccc ccaagctgct gatctacgct gccagctctc tgcagtccgg cgtgccctct     240
agattctccg gctctggctc tggcaccgac tttaccctga ccatcagctc cctgcagccc     300
gaggacttcg ccacctacta ctgtctgcaa gactacagcg ctggaccttc ggccagggc     360 accaaggtgg acatcaagcg gaccgtggcc gcccccagcg tgttcatctt ccctcccagc     420
gacgagcagc tgaagtctgg caccgccagc gtggtgtgcc tgctgaacaa cttctacccc     480
cgcgaggcca aggtgcagtg gaaggtggac aacgccctgc agagcggcaa cagccaggag     540
agcgtgaccg agcaggactc caaggacagc acctacagcc tgagcagcac cctgaccctg     600
agcaaggccg actacgagaa gcacaaggtg tacgcctgcg aggtgaccca ccagggactg     660
tctagccccg tgaccaagag cttcaaccgg ggcgagtgct aa                         702

<210> SEQ ID NO 24
<211> LENGTH: 702
<212> TYPE: DNA
<213> ORGANISM: Artificial Sequence
<220> FEATURE:
<223> OTHER INFORMATION: PG-101 Light Chain Variant 2-hKappa nucleotide
```

```
<400> SEQUENCE: 24
atggagaccg acaccctgct gctctgggtg ctgctgctct gggtgcccgg ctccaccgga        60
gacatccaga tgacccagtc cccctccagc ctgtctgcct ctgtgggcga cagagtgacc       120
atcacctgtc aggcctccca ggacatctcc aactacctga actggtatca gcagaagccc       180
ggcaaggccc ccaagctgct gatctacgct gccagctctc tgcagtccgg cgtgccctct       240
agattctccg gctctggctc tggcaccgac tttaccctga ccatcagctc cctgcagccc       300
gaggacttcg ccacctacta ctgtctgcaa gactacaacc tgtggacctt cggccagggc       360
accaaggtgg acatcaagcg gaccgtggcc gcccccagcg tgttcatctt ccctcccagc       420
gacgagcagc tgaagtctgg caccgccagc gtggtgtgcc tgctgaacaa cttctacccc       480
cgcgaggcca aggtgcagtg gaaggtggac aacgccctgc agagcggcaa cagccaggag       540
agcgtgaccg agcaggactc caaggacagc acctacagcc tgagcagcac cctgaccctg       600
agcaaggccg actacgagaa gcacaaggtg tacgcctgcg aggtgaccca ccagggactg       660
tctagccccg tgaccaagag cttcaaccgg ggcgagtgct aa                         702
```

ANTIBODIES FOR THE TREATMENT OF CANCERS

CROSS REFERENCE TO RELATED APPLICATIONS

This application claims the benefit under 35 U.S.C. § 119(e) of U.S. Provisional Application No. 62/263,561 filed on Dec. 4, 2015, which is incorporated herein by reference in its entirety for all purposes.

GOVERNMENT RIGHTS

This invention was made with Government support under CA163971, awarded by the National Institutes of Health. The Government has certain rights in the invention.

FIELD OF THE INVENTION

This invention relates to anti-EMP2 antibodies, their pharmaceutical compositions and methods for using them in the detection and treatment of cancers that overexpress EMP2, such as triple negative breast cancers and endometrial cancers.

BACKGROUND

The epithelial membrane protein-2 (EMP2) is a member of the growth arrest specific-3/peripheral myelin protein-22 (GAS3/PMP22) family of tetraspan proteins. Other four-transmembrane families, connexins and tetraspanins, play roles in gap junctions, cell-cell recognition processes, and intracellular trafficking. Less is known about the GAS3/PMP22 family. The information available mainly relates to their potential roles in various diseases. For instance, mutations in the prototypic GAS3 family member PMP22 have been found to cause neurodegenerative disease (i.e., Dejerrine Sottas Syndrome and Charcot Marie Tooth Syndrome). EMP2 has also been implicated in B cell tumor progression and stress-induced apoptosis.

EMP2 is expressed at high levels in epithelial cells of the lung, eye, and genitourinary tracts. Like several tetraspan proteins (CD9, CD81, PMP22), EMP2 in murine fibroblasts is localized to lipid raft domains. EMP2 controls cell surface trafficking and function of certain integrins, GPI-linked proteins, and class I MHC molecules, and reciprocally regulates caveolin expression. See, Claas et al., *J Biol Chem* 276:7974-84 (2001); Hasse et al., *J Neurosci Res* 69:227-32 (2002); Wadehra et al., *Exp Mol Pathol* 74:106-12 (2003); Wadehra et al., *Mol Biol Cell* 15:2073-2083 (2004); Wadehra et al., *J Biol Chem* 277:41094-41100 (2002); and Wadehra et al., *Clin Immunol* 107:129-136 (2003).

Endometrial cancer (EC) is the most common gynecological malignancy. In the United States, the death rate from EC has doubled in the last twenty years, and currently a woman has approximately a 3% chance of developing EC during her lifetime (Silverberg et al., *World Health Organization Classification of Tumors: Tumors of the Breast and Female Genital Tract*, Lyon: IARC Press, p. 221-57 (2003); Sorosky J I, *Obstet Gynecol* 111:436-47 (2008)). EC is classified into two major sub-groups based on histology, clinical behavior, and epidemiology. The more common Type I is associated with estrogen predominance and pre-malignant endometrial hyperplasia (Hecht et al., *J Clin Oncol* 24:4783-91 (2006); Sherman, *Mod Pathol* 13:295-308 (2000)). Type II is mediated by non-hormonal risk factors, and often has a high grade or high-risk histology with an aggressive clinical course (Hecht et al., *J Clin Oncol* 24:4783-91 (2006)). Incidence of ECs generally increases with age, with 75-80% of new cases occurring in postmenopausal women (Creasman, *Semin Oncol* 24:S1-140-S1-50 (1997)).

One promising biomarker appears to be EMP2. EMP2 expression is associated with EMP2 neoplasia (Wadehra et al., *Cancer* 107:90-8 (2006)). In endometrial cancer, EMP2 is an independent prognostic indicator for tumors with poor clinical outcome. EMP2 positive tumors, compared to EMP2 negative tumors, had a significantly greater myometrial invasiveness, higher clinical state, recurrent or persistent disease following surgical excision, and earlier mortality. As EMP2 expression was independent of other known biomarkers such as the estrogen receptor and progesterone receptor (Wadehra et al., *Cancer* 107:90-8 (2006)), EMP2 represents a unique biomarker for patients who are not responsive to current hormone or chemotherapy. Moreover, EMP2 expression level positively correlates with the increasing pre-malignant potential of proliferative endometrium. That is, there is a gradation of endometrial EMP2 expression, with minimal expression in normal proliferative or quiescent premenopausal endometrium, and increasing expression in patients with disordered proliferative endometrium, endometrial hyperplasia, and endometrium carcinomas.

Breast cancer remains the most common malignancy among women worldwide. Breast cancer is a heterogeneous disease, which exhibits a wide range of clinical behaviors, prognoses, and histologies (Tavassoli F, Devilee P, editors. (2003) WHO Classification of Tumors. Pathology & Genetics: Tumors of the breast and female genital organs. Lyon (France): IARC Pres). Breast cancer is the abnormal growth of cells that line the breast tissue ducts and lobules and is classified by whether the cancer started in the ducts or the lobules and whether the cells have invaded (grown or spread) through the duct or lobule, and by the way the cells look under the microscope (tissue histology). It is not unusual for a single breast tumor to have a mixture of invasive and in situ cancer.

Molecular classification of breast cancer has identified specific subtypes, often called "intrinsic" subtypes, with clinical and biological implications, including an intrinsic luminal subtype, an intrinsic HER2-enriched subtype (also referred to as the HER2$^+$ or ER$^-$/HER2$^+$ subtype) and an intrinsic basal-like breast cancer (BLBC) subtype. (Perou et al. 2000). Identification of the intrinsic subtypes has typically been accomplished by a combination of methods, including (1) histopathological detection, (2) estrogen receptor (ER), progesterone receptor (PR) and human epidermal growth factor receptor 2 (HER2) expression status and (3) detection of characteristic cellular markers.

Basal-like breast cancer (BLBC), which expresses genes characteristic of basal epithelial cells in the normal mammary gland, comprises up to 15%-25% of all breast cancers (Kreike et al. 2007) and is associated with the worst prognosis of all breast cancer types. BLBCs underexpress estrogen receptor (ER$^-$), progesterone receptor (PR$^-$), and human epidermal growth factor receptor 2 (HER2) and encompass 60% to 90% of so-called "triple negative" (ER$^-$/PR$^-$/HER2$^-$) breast cancers. Although most basal-like breast cancers are often referred to as triple negative based on the expression status of ER, PR and HER2, not all basal-like breast cancers are triple negative.

EMP2 is overexpressed in triple negative breast cancers. EMP2 is a tetraspan protein belonging to the growth arrest specific-3 (GAS3) family. Functionally, EMP2 associates with and modulates the localization and activity of both integrin αvβ3 and focal adhesion kinase (FAK). EMP2 (SEQ ID NO:1) is expressed at high levels in epithelial cells of the lung, eye, and genitourinary tracts. Like several tetraspan proteins (CD9, CD81, PMP22), EMP2 in murine fibroblasts is localized to lipid raft domains. EMP2 controls cell surface trafficking and function of certain integrins, GPI-linked proteins, and class I MHC molecules, and reciprocally regulates caveolin expression. See Claas et al., *J Biol Chem* 276:7974-84 (2001); Hasse et al., *J Neurosci Res* 69:227-32 (2002); Wadehra et al., Exp Mol Pathol 74:106-12 (2003); Wadehra et al., *Mol Biol Cell* 15:2073-2083 (2004); Wadehra et al., *J Biol Chem* 277:41094-41100 (2002); and Wadehra et al., *Clin Immunol* 107:129-136 (2003).

SEQ ID NO:1 (ACCESSION P54851) MLVLLAFIIA FHITSAALLF IATVDNAWWV GDEFFADVWR ICTNNTNCTV INDSFQEYST LQAVQATMIL STILC-CIAFF IFVLQLFRLK QGERFVLTSI IQLMSCLCVM IAASIYTDRR EDIHDKNAKF YPVTREGSYG YSYILAWVAF ACTFISGMMY LILRKRK

EMP2 appears to regulate trafficking of various proteins and glycolipids by facilitating transfer of molecules from post-Golgi endosomal compartments to appropriate plasma membrane locations. Specifically, EMP2 is thought to facilitate the appropriate trafficking of select molecules into glycolipids-enriched lipid raft microdomains (GEMs) (Wadehra et al., Mol Biol Cell 15:2073-83 (2004)). GEMs are cholesterol rich microdomains which are often associated with chaperones, receptosomes, and protein complexes that are important for efficient signal transduction (Leitinger et al., J Cell Sci 115:963-72 (2002); Moffett et al., J Biol Chem 275:2191-8 (2000)). Moreover, GEMs are involved in correct sorting of proteins from the Golgi apparatus to plasma membrane (Abrami et al., J Biol Chem 276:30729-36 (2001); Galbiati et al., Cell 106:403-11 (2001); Gruenberg et al., Curr Opin Cell Biol 7: 552-63 (1995)). In this respect, modulation of EMP2 expression levels or its location on the plasma membrane alters the surface repertoire of several classes of molecules including integrins, focal adhesion kinase, class I major histocompatibility molecules and other immunoglobulin super-family members such as CD54 and GPI-linked proteins (Wadehra et al., Dev Biol 287:336-45 (2005); Wadehra et al., Clinical Immunology 107:129-36 (2003); Morales et al., Invest Opthalmol Vis Sci (2008)).

EMP2 expression is associated with EMP2 neoplasia (Wadehra et al., Cancer 107:90-8 (2006)). In endometrial cancer, for example, EMP2 is an independent prognostic indicator for tumors with poor clinical outcome. EMP2 positive tumors, compared to EMP2 negative tumors, had a significantly greater myometrial invasiveness, higher clinical state, recurrent or persistent disease following surgical excision, and earlier mortality.

It has been previously shown that EMP2 can be used as a target in the treatment of cancers that express or overexpress EMP2, such as triple negative breast cancer and endometrial cancer. As discussed above, there remains a large need for other novel methods and compositions which are useful in the prevention, treatment, and modulation of such EMP2 expression cancers. Accordingly, provided herein are novel compositions and methods for meeting these and other needs.

BRIEF SUMMARY

Provided herein are novel anti-EMP2 antibodies useful for the treatment and diagnosis of cancers that express or overexpress EMP2.

In one aspect, provided herein is an isolated antibody that binds to Epithelial Membrane Protein 2 (EMP2), that includes heavy chain variable region and a light chain variable region. The heavy chain variable region includes three heavy chain complementary determining regions (HCDRs) and the light chain variable region includes three light chain variable regions (LCDRs). In some embodiments, the sequence of HCDR1 is SEQ ID NO:11, the sequence of HCDR2 is SEQ ID NO:12, the sequence of HCDR3 is SEQ ID NO:13, the sequence of LCDR1 is SEQ ID NO:14, the sequence of LCDR2 is SEQ ID NO:15, and the sequence of LCDR3 is SEQ ID NO:16.

In some embodiments, the heavy chain variable region includes an amino acid sequence that shares 90% sequence identity with SEQ ID NO:3 and the light chain variable region includes an amino acid sequence that shares 90% sequence identity SEQ ID NO:4 or SEQ ID NO:5.

In certain embodiments, the antibody includes the heavy chain variable region comprising the amino acid sequence according to SEQ ID NO:3 and the light chain variable region comprising the amino acid sequence according to SEQ ID NO:4. In some embodiments, the antibody includes a heavy chain comprising the amino acid sequence according to SEQ ID NO:6 and a light chain comprising the amino acid sequence to SEQ ID NO:7.

In some embodiments, the antibody comprises the heavy chain variable region comprising the amino acid sequence according to SEQ ID NO:3 and the light chain variable region comprising the amino acid sequence according to SEQ ID NO: 5. In certain embodiments, the antibody includes a heavy chain comprising the amino acid sequence according to SEQ ID NO:6 and a light chain comprising the amino acid sequence to SEQ ID NO:8.

In exemplary embodiments, the antibody is a monoclonal antibody, a humanized monoclonal antibody, a human antibody, a diabody, minibody, or triabody, a chimeric antibody, or a recombinant antibody. In some embodiments, the antibody is in an scFv, minibody, diabody, or triabody format. In certain embodiments, the subject antibody is conjugated to a cytotoxic agent or a label.

In another aspect, provided herein is a pharmaceutical composition that includes any one of the subject antibodies provided herein and a physiologically acceptable carrier.

In another aspect, provided herein is a method of treating or reducing the rate of reoccurrence of a cancer in a patient. The method includes administering to the patient an effective amount of an anti-EMP2 antibody comprising a heavy chain variable region and a light chain variable region. The heavy chain variable region includes three heavy chain complementary determining regions (HCDRs) and the light chain variable region includes three light chain variable regions (LCDRs). In exemplary embodiments, the sequence of HCDR1 is SEQ ID NO:11, the sequence of HCDR2 is SEQ ID NO:12, the sequence of HCDR3 is SEQ ID NO:13, the sequence of LCDR1 is SEQ ID NO:14, the sequence of LCDR2 is SEQ ID NO:15, and the sequence of LCDR3 is SEQ ID NO:16.

In certain embodiments, the heavy chain variable region includes an amino acid sequence that shares 90% sequence identity with SEQ ID NO:3 and the light chain variable region comprises an amino acid sequence that shares 90% sequence identity SEQ ID NO:4 or SEQ ID NO:5.

In some embodiments, the antibody includes the heavy chain variable region comprising the amino acid sequence according to SEQ ID NO:3 and the light chain variable region comprising the amino acid sequence according to SEQ ID NO:4. In certain embodiments, the antibody includes a heavy chain comprising the amino acid sequence according to SEQ ID NO:6 and a light chain comprising the amino acid sequence to SEQ ID NO:7.

In some embodiments, the antibody includes the heavy chain variable region comprising the amino acid sequence according to SEQ ID NO:4 and light chain variable region comprising the amino acid sequence according to SEQ ID NO:5. In certain embodiments, the antibody includes a heavy chain comprising the amino acid sequence according to SEQ ID NO:6 and a light chain comprising the amino acid sequence to SEQ ID NO:8.

In certain embodiments, the method includes the step of detecting cancer stem cells in a patient that express EMP2 and one or more markers selected from the group consisting of CD44, CD133 ABCG2, and ALDH prior to the administering step.

In some embodiments of the subject method, the antibody further includes a physiological acceptable carrier or a pharmaceutically acceptable carrier.

In certain embodiments, the method includes administering to the patient an effective amount of at least one additional anti-cancer agent. In exemplary embodiments, the at least one additional anti-cancer agent is selected from the group consisting of platinum-based chemotherapy drugs, taxanes, tyrosine kinase inhibitors, anti-EGFR antibodies, anti-ErbB2 antibodies, and combinations thereof.

In certain embodiments, the least one additional anti-cancer agent comprises a VEGF inhibitor. In some embodiments, the VEGF inhibitor comprises an anti-VEGF antibody. In certain embodiments, the anti-VEGF antibody is bevacizumab.

In certain embodiments, the at least one additional anti-cancer agent includes an EGFR inhibitor. In certain embodiments, the EGFR inhibitor comprises an anti-EGFR antibody. In some embodiments, the anti-EGFR antibody comprises cetuximab. In exemplary embodiments, the anti-EGFR antibody is selected from the group consisting of matuzumab, panitumumab, and nimotuzumab. In some embodiments, the EGFR inhibitor is a small molecule inhibitor of EGFR signaling. In certain embodiments, the small molecule inhibitor of EGFR signaling is selected from the group consisting of gefitinib, lapatinib, canertinib, pelitinib, erlotinib HCL, PKI-166, PD158780, and AG 1478.

In some embodiments of the subject method, the antibody is conjugated with an effector moiety. In certain embodiments, the effector moiety is a toxic agent. In some embodiments, the toxic agent is such as ricin.

In certain embodiments of the subject method, the treatment includes blocking invasiveness of the cancer.

In some embodiments, the subject antibodies are used in vaccine therapies for the cancer. In some embodiments, the patient is human or mammal.

In some embodiments of the subject methods, the cancer is breast cancer. In certain embodiments of the subject methods, the cancer is a cancer selected from a group comprising brain cancer, colon cancer, melanoma, leukemia (e.g., AML), pancreatic cancer, prostate cancer, ovarian cancer, lung cancer, and gastric cancer.

In some embodiments of the subject methods, the method includes a companion diagnostic. In certain embodiments, the companion diagnostic includes an anti-EMP2 antibody.

In another aspect, provided herein is a method of detecting cancer stem cells, the method includes obtaining a biological sample derived from a human having or suspected of having cancer; and detecting the expression EMP2. In some embodiments, the method further includes deteting the expression of one or more markers selected from the group consisting of CD44, CD133, ABCG2, and ALDH.

In some embodiments, the detecting is performed using an anti-EMP2 antibody that includes a heavy chain variable region and a light chain variable region. The heavy chain variable region includes three heavy chain complementary determining regions (HCDRs) and wherein the light chain variable region includes three light chain variable regions (LCDRs), wherein: the sequence of HCDR1 is SEQ ID NO:11, the sequence of HCDR2 is SEQ ID NO:12, the sequence of HCDR3 is SEQ ID NO:13, the sequence of LCDR1 is SEQ ID NO:14, the sequence of LCDR2 is SEQ ID NO:15, and the sequence of LCDR3 is SEQ ID NO:16.

In certain embodiments of the method of detecting, the human has or is suspected of having a cancer. In particular embodiments, the cancer is a breast cancer. In exemplary embodiments, the human has or is suspected of having triple negative breast cancer. In other embodiments, the human has or is suspected of having endometrial cancer.

BRIEF DESCRIPTION OF THE DRAWINGS

FIG. 5 include graphs, showing the ability of the PG-101 vs. Variant 1 to induce cell death. Left, cell death was measured by quantitating annexin V/propidium iodide staining using flow cytometry. Right, total cell numbers following incubation for 5 days were enumerated using trypan blue exclusion.

FIG. 8 includes two graphs showing the ability of anti-EMP2 antibodies to reduce ALDH activity, a measure of cancer stem cells, in two independent experiments.

FIG. 10 shows raw images of cells post incubation of control IgG, PG-101, or variant 1 were incubated for 2 weeks with BT474 cells. FIG. 11 shows enumeration of mammospheres in triplicate wells. *, p<0.05 using Student's t test.

FIG. 13 shows a summary of a trypsin cleavage experiment to identify whether potential PG-101 deamidation sites were susceptible to cleavage. In order to confirm the sequence liability, PG-101 was cleaved using trypsin and then subjected to mass-spectometry. Mass spec confirmed that the predicted site in the CDR3 was susceptibility to cleavage.

DETAILED DESCRIPTION

Introduction

Figure 1:
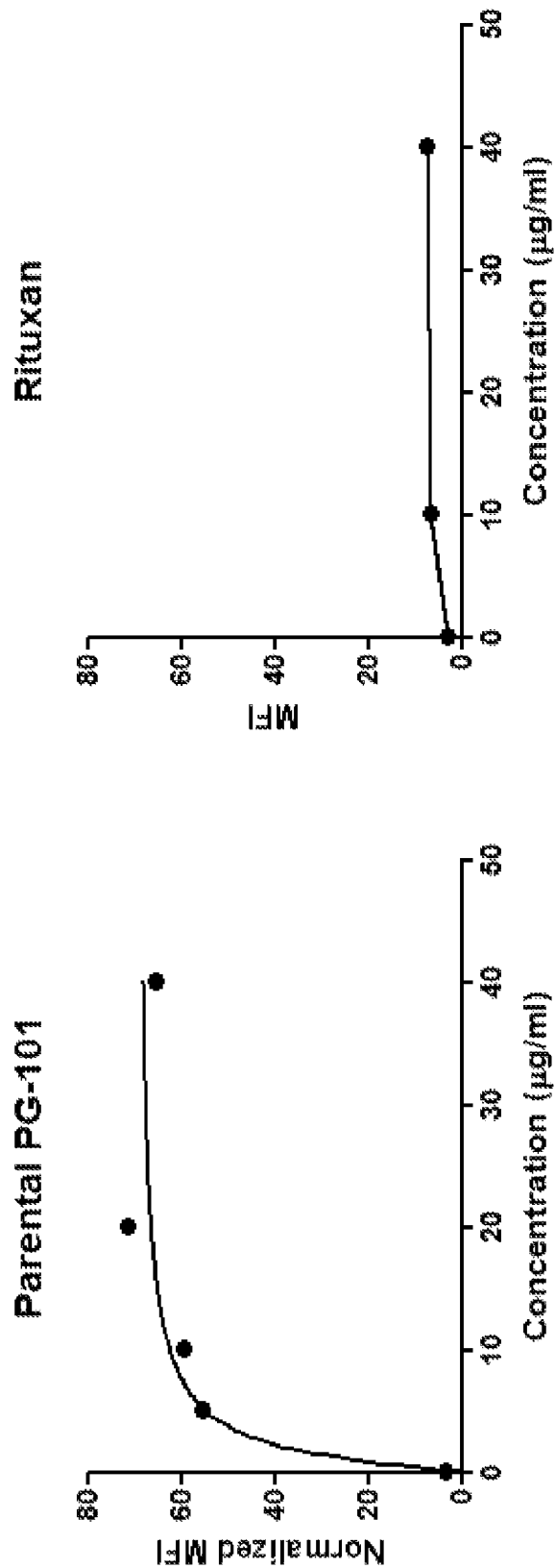
FIG. 1 includes graphs, showing the titration of anti-EMP2 IgG1 antibodies on SUM149 cells. Left, reformulation of PG-101 was tested on SUM149 cells by measuring its binding using flow cytometry. Right, to confirm the specificity and sensitivity of binding, rituximab was utilized as a negative control.

Previously, it has been shown that treatment human endometrial adenocarcinoma cell lines with anti-EMP2 diabodies was found to induce significant cell death and caspase 3 cleavage in vitro. See, e.g., US Pat. Pub. 20100272732. These responses correlated with cellular EMP2 expression, and were augmented by progesterone (which physiologically induces EMP2 expression). In vivo, treatment of subcutaneous human xenografts of HEC-1A cell lines with anti-EMP2 diabodies suppressed tumor growth, and induced striking xenograft cell death. It has also previously reported that targeting of EMP2 may offer a therapeutic strategy in treating breast cancer. See, e.g., US Pat. Pub. 20100272732, incorporated by reference in its entirety. Accordingly provided herein are novel anti-EMP2 antibodies, their pharmaceutical compositions and method of treatment and diagnosis of cancers, such as endometrial cancers and breast cancers, using such novel anti-EMP2 antibodies. The antibodies provided herein exhibit increased binding affinity to the second extracellular loop of EMP2 compared to existing anti-EMP2 antibodies, while exhibiting at least similar stability compared to such existing anti-EMP2 antibodies.

Accordingly, in its first aspect, provided herein are novel anti-EMP2 antibodies and methods of treating cancer (e.g., endometrial cancer and breast cancer). In another aspect, the invention provides compositions of anti-EMP2 antibodies and methods of detecting such cancers (e.g., triple negative breast cancer and endometrial cancer). In another aspect, the invention provides compositions of anti-EMP2 antibodies and methods of co-administration with one or more additional therapies. In another aspect, the invention provides companion diagnostic methods and products for use with the methods and antibodies described herein.

Antibodies

Antibodies that find use in the present invention can take on a number of formats such as traditional antibodies as well as antibody derivatives, fragments and mimetics. In certain embodiments, the antibody is an anti-EMP2 antibody that includes a heavy chain variable domain and a light chain variable domain. In some embodiments, the heavy chain variable domain includes any of the heavy chain variable domain described herein and the light chain variable domain includes any of the light chain variable domains described herein. In certain embodiments, the anti-EMP2 antibody includes a heavy chain and light chain, where the heavy chain is any of the heavy chains described herein and the light chain is any light chain described herein.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of isotypes and/or subclasses.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5$^{th}$ Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk, *J. Mol. Biol.* 196:901-917 (1987). Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. For example, as described herein the antibodies bind to an epitope in the presumptive second extracellular domain of EMP2.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

In some embodiments, the epitope is derived from SEQ ID NO:2, wherein SEQ ID NO:2 is EDIHDKNAKFYPVTREGSYG and represents a 20-mer polypeptide sequence from the second extracellular loop of human EMP2.

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that still rely In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

In some embodiments, the antibody can be a mixture from different species, e.g. a chimeric antibody and/or a humanized antibody. That is, in the present invention, the CDR sets can be used with framework and constant regions other than those specifically described by sequence herein.

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibodies of the invention can be multispecific antibodies, and notably bispecific antibodies. These are antibodies that bind to two (or more) different antigens, or different epitopes on the same antigen.

In some embodiments the antibodies are diabodies.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

The antibodies described herein can be isolated or recombinant. An "isolated antibody," refers to an antibody which is substantially free of other antibodies having different antigenic specificities. For instance, an isolated antibody that specifically binds to EMP2 is substantially free of antibodies that specifically bind antigens other than EMP2.

An isolated antibody that specifically binds to an epitope, isoform or variant of human EMP2 or murine EMP2 may, however, have cross-reactivity to other related antigens, for instance from other species, such as EMP2 species homologs. Moreover, an isolated antibody may be substantially free of other cellular material and/or chemicals.

Anti-EMP2 variable region sequences, used to encode proteins on backbones including for native antibody, fragment antibody, or synthetic backbones, can avidly bind EMP-2. Via this binding, these proteins can be used for EMP2 detection, and to block EMP2 function. Expression of these variable region sequences on native antibody backbones, or as an scFv, triabody, diabody or minibody, labeled with radionuclide, are particularly useful in in the in vivo detection of EMP-2 bearing cells. Expression on these backbones or native antibody backbone are favorable for blocking the function of EMP-2 and/or killing EMP-2 bearing cells (e.g., gynecologic tumors) in vivo.

The anti-EMP2 antibodies of the present invention specifically bind EMP2 ligands (e.g. the human and murine EMP2 proteins of SEQ ID NOs:1 and 2).

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

In some embodiments, the antibody provided herein includes a heavy chain variable region that includes an amino acid sequence that shares at least 60%, 65%, 70%, 75%, 80%, 85%, 90%, 95%, 99% or more sequence identity with SEQ ID NO:3 and a light chain variable region that includes an amino acid sequence that shares at least 60%, 65%, 70%, 75%, 80%, 85%, 90%, 95%, 99% or more sequence identity with SEQ ID NO:4 or SEQ ID NO:5, as shown below:

```
                                          (SEQ ID NO 3)
QVQLVQSGGGVVQPGRSLRLSCAASGFTFSSYAMHWVRQAPGKGLEWVAV

ISYDGSNKYYADSVKGRFTISRDNSKNTLYLQMNSLRAEDTAVYYCARDR

RGRKSAGIDYWGQGTLVTVSS. PG-101 heavy chain variable region domain.

(SEQ ID NO: 4)
DIQMTQSPSSLSASVGDRVTITCQASQDISNYLNWYQQKPGKAPKLLIYA

ASSLQSGVPSRFSGSGSGTDFTLTISSLQPEDFATYYCLQDYSGWTFGQG

TKVDIK. PG-101 variant 1 light chain variable region domain.
```

```
                                                   (SEQ ID NO: 5)
DIQMTQSPSSLSASVGDRVTITCQASQDISNYLNWYQQKPGKAPKLLIYA

ASSLQSGVPSRFSGSGSGTDFTLTISSLQPEDFATYYCLQDYNLWTFGQG

TKVDIK. PG-101 Variant 2 light chain variable region domain.
```

As described herein, such anti-EMP2 antibodies are variant anti-EMP2 antibodies that advantageously exhibit increased epitope (SEQ ID NO:2) binding compared to known anti-EMP2 antibodies.

In some embodiments, the antibody includes a heavy chain variable region that includes an amino acid sequence sharing at least 60%, 65%, 70%, 75%, 80%, 85%, 90%, 95%, 99% or more sequence identity with SEQ ID NO:3 and a light chain variable region that includes an amino acid sequence sharing at least 60%, 65%, 70%, 75%, 80%, 85%, 90%, 95%, 99% or more sequence identity with SEQ ID NO:4. In some embodiments, the antibody includes a heavy chain variable region having the amino acid sequence as set forth in SEQ ID NO:3 and a light chain variable region having the amino acid sequence as set forth in SEQ ID NO:4.

In some embodiments, the antibody includes a heavy chain that shares at least 60%, 65%, 70%, 75%, 80%, 85%, 90%, 95%, 99% or more sequence identity with the amino acid sequence according to SEQ ID NO:6 and a light that shares at least 60%, 65%, 70%, 75%, 80%, 85%, 90%, 95%, 99% or more sequence identity with the amino acid sequence according to SEQ ID NO:7. In some embodiments, the antibody includes a heavy chain having an amino acid sequence according to SEQ ID NO:6 and a light chain having an amino acid sequence according to SEQ ID NO:7.

```
                                                   (SEQ ID NO: 6)
QVQLVQSGGGVVQPGRSLRLSCAASGFTFSSYAMHWVRQAPGKGLEWVAV

ISYDGSNKYYADSVKGRFTISRDNSKNTLYLQMNSLRAEDTAVYYCARDR

RGRKSAGIDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSP

G. PG-101 heavy chain.
                                                   (SEQ ID NO: 7)
DIQMTQSPSSLSASVGDRVTITCQASQDISNYLNWYQQKPGKAPKLLIYA

ASSLQSGVPSRFSGSGSGTDFTLTISSLQPEDFATYYCLQDYSGWTFGQG

TKVDIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC. PG-101 variant 1 light chain.
```

In some embodiments, the antibody includes a heavy chain variable region that includes an amino acid sequence sharing at least 60%, 65%, 70%, 75%, 80%, 85%, 90%, 95%, 99% or more sequence identity with SEQ ID NO:3 and a light chain variable region that includes an amino acid sequence sharing at least 60%, 65%, 70%, 75%, 80%, 85%, 90%, 95%, 99% or more sequence identity with SEQ ID NO:5. In some embodiments, the antibody includes a heavy chain variable region having the amino acid sequence as set forth in SEQ ID NO:3 and a light chain variable region having the amino acid sequence as set forth in SEQ ID NO:5.

In some embodiments, the antibody includes a heavy chain that shares at least 60%, 65%, 70%, 75%, 80%, 85%, 90%, 95%, 99% or more sequence identity with the amino acid sequence according to SEQ ID NO:6 and a light that shares at least 60%, 65%, 70%, 75%, 80%, 85%, 90%, 95%, 99% or more sequence identity with the amino acid sequence according to SEQ ID NO:8. In some embodiments, the antibody includes a heavy chain having an amino acid sequence according to SEQ ID NO:6 and a light chain having an amino acid sequence according to SEQ ID NO:8.

```
                                                   (SEQ ID NO: 8)
DIQMTQSPSSLSASVGDRVTITCQASQDISNYLNWYQQKPGKAPKLLIYA

ASSLQSGVPSRFSGSGSGTDFTLTISSLQPEDFATYYCLQDYNLWTFGQG

TKVDIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC. PG-101 Variant 2 light chain.
```

In some embodiments, the antibody includes a heavy chain variable region that includes an amino acid sequence sharing at least 60%, 65%, 70%, 75%, 80%, 85%, 90%, 95%, 99% or more sequence identity with SEQ ID NO:3 and a light chain variable region that includes an amino acid sequence sharing at least 60%, 65%, 70%, 75%, 80%, 85%, 90%, 95%, 99% or more sequence identity with SEQ ID NO:9. In some embodiments, the antibody includes a heavy chain variable region having the amino acid sequence as set forth in SEQ ID NO:3 and a light chain variable region having the amino acid sequence as set forth in SEQ ID NO:9.

```
                                                   (SEQ ID NO: 9)
DIQMTQSPSSLSASVGDRVTITCQASQDISNYLNWYQQKPGKAPKLLIYA

ASSLQSGVPSRFSGSGSGTDFTLTISSLQPEDFATYYCLQDYNGWTFGQG

TKVDIK. PG-101 parental light chain variable region domain.
```

In some embodiments, the antibody includes a heavy chain that shares at least 60%, 65%, 70%, 75%, 80%, 85%, 90%, 95%, 99% or more sequence identity with the amino acid sequence according to SEQ ID NO:6 and a light that shares at least 60%, 65%, 70%, 75%, 80%, 85%, 90%, 95%, 99% or more sequence identity with the amino acid sequence according to SEQ ID NO:10. In some embodiments, the antibody includes a heavy chain having an amino acid sequence according to SEQ ID NO:6 and a light chain having an amino acid sequence according to SEQ ID NO:10.

```
                                                  (SEQ ID NO: 10)
DIQMTQSPSSLSASVGDRVTITCQASQDISNYLNWYQQKPGKAPKLLIYA

ASSLQSGVPSRFSGSGSGTDFTLTISSLQPEDFATYYCLQDYNGWTFGQG
```

```
TKVDIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC. PG-101 parental light chain.
```

In some embodiments, the anti-EMP2 comprises a heavy chain variable domain that includes a HCDR1 according to SEQ ID NO:11, a HCDR2 according to SEQ ID NO:12, a HCDR3 according to SEQ ID NO:13 and a light chain variable domain that includes a LCDR1 according to SEQ ID NO:14, a LCDR2 according to SEQ ID NO:15 and a LCDR3 according to SEQ ID NO:16, as depicted below. As shown in the studies provided herein, anti-EMP2 antibodies having such CDRs advantageously exhibit increased binding to EMP2 as well as stability as least comparable to known anti-EMP2 antibodies.

```
Variable heavy chain CDR1:
                          (SEQ ID NO: 11)
SYAMH

Variable heavy chain CDR2:
                          (SEQ ID NO: 12)
VISYDGSNKYYADSVKG Variable heavy chain CDR3:
                          (SEQ ID NO: 13)
DRRGRKSAGIDY Variable light chain CDR1:
                          (SEQ ID NO: 14)
QASQDISNYLN Variable light chain CDR2:
                          (SEQ ID NO: 15)
AASSLQS Variable light chain CDR3:
                          (SEQ ID NO: 16)
LQDYSGWT
```

The present invention further provides variant antibodies. That is, there are a number of modifications that can be made to the antibodies of the invention, including, but not limited to, amino acid modifications in the CDRs (affinity maturation), amino acid modifications in the Fc region, glycosylation variants, covalent modifications of other types, etc. The CDRs of the subject antibodies provided herein are as follows:

By "variant" herein is meant a polypeptide sequence that differs from that of a parent polypeptide by virtue of at least one amino acid modification. Amino acid modifications can include substitutions, insertions and deletions, with the former being preferred in many cases.

In general, variants can include any number of modifications, as long as the function of the protein is still present, as described herein. That is, in the case of amino acid variants generated with the heavy or light chain variable regions described herein, for example, the antibody should still specifically bind to both human and/or murine EMP2. Similarly, if amino acid variants are generated with the Fc region, for example, the variant antibodies should maintain the required receptor binding functions for the particular application or indication of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications, with from 1-2, 1-3 and 1-4 also finding use in many embodiments.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 95% or up to 98 or 99% identity to the parent sequences. It should be noted that depending on the size of the sequence, the percent identity will depend on the number of amino acids.

By "amino acid substitution" or "substitution" herein is meant the replacement of an amino acid at a particular position in a parent polypeptide sequence with another amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, *Biotechnology* 10:779-783 that describes affinity maturation by heavy chain variable region (VH) and light chain variable region (VL) domain shuffling. Random mutagenesis of CDR and/or framework residues is described in: Barbas, et al. 1994, *Proc. Nat. Acad. Sci, USA* 91:3809-3813; Shier et al., 1995, *Gene* 169:147-155; Yelton et al., 1995, *J. Immunol.* 155:1994-2004; Jackson et al., 1995, *J. Immunol.* 154(7): 3310-9; and Hawkins et al, 1992, *J. Mol. Biol.* 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of the subject antibodies described herein (SEQ ID NOS:11 to 16). In addition, as outlined below, amino acid modifications can also independently and optionally be made in any region outside the CDRs, including framework and constant regions.

In some embodiments, the anti-EMP2 antibodies provided herein are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341,769, U.S. Pat. Nos. 6,737,056, 7,670,600, 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deaminated to the corresponding glutamyl and aspartyl residues, respectively. Alternatively, these residues are deaminated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, N.J.]; GlycoMAb® glycosylation engineering technology [Glycart Biotechnology AG, Zürich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In some cases, one or more of the components of the competitive binding assays are labeled.

It may also be the case that competition may exist between anti-EMP2 antibodies with respect to more than one of EMP2 epitope, and/or a portion of EMP2, e.g. in a context where the antibody-binding properties of a particular region of EMP2 are retained in fragments thereof, such as in the case of a well-presented linear epitope located in various tested fragments or a conformational epitope that is presented in sufficiently large EMP2 fragments as well as in EMP2.

Assessing competition typically involves an evaluation of relative inhibitory binding using an antibody of the invention, EMP2 (either human or murine or both), and the test molecule. Test molecules can include any molecule, including other antibodies, small molecules, peptides, etc. The compounds are mixed in amounts that are sufficient to make a comparison that imparts information about the selectivity and/or specificity of the molecules at issue with respect to the other present molecules.

The amounts of test compound, EMP2 and antibodies of the invention may be varied. For instance, for ELISA assessments about 5-50 µg (e.g., about 10-50 µg, about 20-50 µg, about 5-20 µg, about 10-20 µg, etc.) of the anti-EMP2 antibody and/or EMP2 targets are required to assess whether competition exists. Conditions also should be suitable for binding. Typically, physiological or near-physiological conditions (e.g., temperatures of about 20-40° C., pH of about 7-8, etc.) are suitable for anti-EMP2:EMP2 binding.

Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to EMP2 (e.g., the natural binding partners of EMP2 or naturally occurring anti-EMP2 antibody).

In some embodiments, the anti-EMP2 antibody of the present invention specifically binds to one or more residues or regions in EMP2 but also does not cross-react with other proteins with homology to EMP2.

Typically, a lack of cross-reactivity means less than about 5% relative competitive inhibition between the molecules when assessed by ELISA and/or FACS analysis using sufficient amounts of the molecules under suitable assay conditions.

The disclosed antibodies may find use in blocking a ligand-receptor interaction or inhibiting receptor component interaction. The anti-EMP2 antibodies of the invention may be "blocking" or "neutralizing." A "neutralizing antibody" is intended to refer to an antibody whose binding to EMP2 results in inhibition of the biological activity of EMP2, for example its capacity to interact with ligands, enzymatic activity, and/or signaling capacity. Inhibition of the biological activity of EMP2 can be assessed by one or more of several standard in vitro or in vivo assays known in the art.

Inhibits binding" or "blocks binding" (for instance when referring to inhibition/blocking of binding of a EMP2 binding partner to EMP2) encompass both partial and complete inhibition/blocking. The inhibition/blocking of binding of a EMP2 binding partner to EMP2 may reduce or alter the normal level or type of cell signaling that occurs when a EMP2 binding partner binds to EMP2 without inhibition or blocking. Inhibition and blocking are also intended to include any measurable decrease in the binding affinity of a EMP2 binding partner to EMP2 when in contact with an anti-EMP2 antibody, as compared to the ligand not in contact with an anti-EMP2 antibody, for instance a blocking of binding of a EMP2 binding partner to EMP2 by at least about 10%, 20%, 30%, 40%, 50%, 60%, 70%, 80%, 90%, 99%, or 100%.

The present invention further provides methods for producing the disclosed anti-EMP2 antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

In general, nucleic acids are provided that encode the antibodies of the invention (see, e.g., SEQ ID NOS:21 to 24). Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

The anti-EMP2 antibodies provided herein can further include a label or detectable moiety attached thereto. A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

Compositions

When used for pharmaceutical purposes, the anti-EMP2 antibodies provided herein are typically formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al., *Biochemistry* 5:467 (1966). The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids or polypeptides of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in Remington's *Pharmaceutical Sciences*, Mack Publishing Company, Philadelphia, Pa., 17th ed. (1985).

The pharmaceutical compositions according to the invention comprise a therapeutically effective amount of a subject anti-EMP2 antibody and a pharmaceutically acceptable carrier. By "therapeutically effective dose or amount" herein is meant a dose that produces effects for which it is administered (e.g., treatment or prevention of a cancer). The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); *Remington: The Science and Practice of Pharmacy*, 20th Edition, Gennaro, Editor (2003), and Pickar, *Dosage Calculations* (1999)). The EMP2 *Chlamydia* inhibitor, if a salt, is formulated as a "pharmaceutically acceptable salt."

A "pharmaceutically acceptable salt" or to include salts of the active compounds which are prepared with relatively nontoxic acids or bases, according to the route of administration. When inhibitors of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Aside from biopolymers such as nucleic acids and polypeptides, certain compounds of the present invention possess asymmetric carbon atoms (optical centers) or double bonds; the racemates, diastereomers, geometric isomers and individual isomers are all intended to be encompassed within the scope of the present invention. In preferred embodiments, wherein the compound comprises amino acids or nucleic acids, the amino acids and nucleic acids are each the predominant naturally occurring biological enantiomer.

The compositions for administration will commonly comprise an agent as described herein dissolved in a pharmaceutically acceptable carrier, preferably an aqueous carrier.

A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Suitable formulations for use in the present invention are found in *Remington: The Science and Practice of Pharmacy*, 20th Edition, Gennaro, Editor (2003) which is incorporated herein by reference. Moreover, for a brief review of methods for drug delivery, see, Langer, *Science* 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the anti-EMP2 antibodies provided herein can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the anti-EMP2 antibodies provided herein can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

In some embodiments, a pharmaceutical composition for intravenous administration may provide from about 0.1 to 100 mg per patient per day. Dosages from 0.1 up to about 100 mg per patient per day may be used. Substantially higher dosages are possible in topical administration. Actual methods for preparing parenterally administrable compositions will be known or apparent to those skilled in the art and are described in more detail in such publications as *Remington: The Science and Practice of Pharmacy*, 21st Edition 2005, Lippincott Williams & Wilkins, Publishers.

The pharmaceutical compositions can be administered in a variety of dosage forms and amounts depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations can be prepared by mixing anti-EMP2 antibody having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e. g. Zn-protein complexes); and/or non-ionic surfactants. The antibody can be formulated at a concentration of between 0.5-200 mg/ml, or between 10-50 mg/ml.

The compositions containing the subject anti-EMP2 antibodies can be administered for therapeutic or prophylactic treatments. In therapeutic applications, compositions are administered to a patient in a "therapeutically effective dose." Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The pharmaceutical compositions can comprise additional active agents, including any one or more of the following, analgesics, anti-inflammatories, antibiotics, antimicrobials, lubricants, contraceptives, spermicides, local anesthetics, and anti-puritics.

As used herein, the term "carrier" refers to a typically inert substance used as a diluent or vehicle for an active agent to be applied to a biological system in vivo or in vitro. (e.g., drug such as a therapeutic agent). The term also encompasses a typically inert substance that imparts cohesive qualities to the composition.

In some embodiments, the invention provides a composition comprising an EMP2 inhibitor and a physiologically acceptable carrier at the cellular or organismal level. Typically, a physiologically acceptable carrier is present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., *Remington's Pharmaceutical Sciences*, 17$^{th}$ ed., 1989). The carriers and compositions are preferably sterile.

The compositions provided herein may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically or physiologically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based drug suspended in diluents, e.g., water, saline, or PEG 400; (b) capsules, sachets, or tablets, each containing a predetermined amount of a platinum-based drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

Methods of Treatment

In another aspect, provided herein is a method of treating a cancer (e.g., an invasive cancer or a metastasis), preventing the progression of an EMP-2 expressing cancer or reducing the rate of a cancer in a subject by administering to the subject an effective amount of any one of the subject anti-EMP2 antibodies described herein or an immunoconjugate that includes a subject anti-EMP2 antibody. In some embodiments, the subject is a mammalian subject. In certain embodiments, the subject is a human. In exemplary embodiments, the subject is at least 20 years, 25 years, 30 years, 35 years, 40 years, 45 years, 50 years, 55 years, 60 years, 65 years, 70 years, 75 years, 80 years, 85 years, 90 years, 95 years or 100 years of age.

As used herein, "cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma. "Urogenital cancer" refers to human cancers of urinary tract and genital tissues, including but not limited to kidney, bladder, urinary tract, urethra, prostrate, penis, testicle, vulva, vagina, cervical and ovary tissues. The cancers to be detected, diagnosed or treated herein express or overexpress EMP2. Cancers which overexpress EMP2 include, but are not limited to, endometrial cancer, ovarian cancer, glioblastoma, breast cancer, prostate cancer, testicular cancer, and myeloma.

In some embodiments, the methods provided herein are for the treatment of a therapy resistant cancer. "Therapy resistant" cancers, tumor cells, and tumors refers to cancers that have become resistant or refractory to either or both apoptosis-mediated (e.g., through death receptor cell signaling, for example, Fas ligand receptor, TRAIL receptors, TNF-R1, chemotherapeutic drugs, radiation) and non-apoptosis mediated (e.g., toxic drugs, chemicals) cancer therapies, including chemotherapy, hormonal therapy, radiotherapy, and immunotherapy. The invention contemplates treatment of both types.

In some embodiments, the subject methods provided herein are for the treatment of cancers that overexpress EMP2. "Overexpression" refers to RNA or protein expression of EMP2 in a tissue that is significantly higher that RNA or protein expression of in a control tissue sample. In one embodiment, the tissue sample is autologous. Cancerous test tissue samples associated with invasiveness, metastasis, hormone independent (e.g., androgen independence), or refractoriness to treatment or an increased likelihood of same typically have at least two fold higher expression of EMP2 mRNA or protein, often up to three, four, five, eight, ten or more fold higher expression of EMP2 protein in comparison to cancer tissues from patients who are less likely to progress to metastasis or to normal (i.e., non-cancer) tissue samples. Such differences may be readily apparent when viewing the bands of gels with approximately similarly loaded with test and controls samples. Prostate cancers expressing increased amounts of EMP2 are more likely to become invasive, metastasize, or progress to treatment refractory cancer. Various cutoffs are pertinent for EMP2 overexpression, since it is possible that a small percentage of EMP2 positive cells in primary tumors may identify tumors with a high risk for recurrence and metastasis. The terms "overexpress," "overexpression" or "overexpressed" interchangeably refer to a gene that is transcribed or translated at a detectably greater level, usually in a cancer cell, in comparison to a normal cell of the same type.

Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more (2-fold, 3-fold, 4-fold) in comparison to a non-cancerous cell of the same type. The overexpression may be based upon visually detectable or quantifiable differences observed using immunohistochemical methods to detect EMP2 protein or nucleic acid. The terms "cancer that overexpresses EMP2" and "cancer associated with the overexpression of EMP2" interchangeably refer to cancer cells or tissues that overexpress EMP2 in accordance with the above definition.

In some embodiments, the method includes the administration of an immunoconjugate to the subject. The immunoconjugate can include a subject anti-EMP2 antibody or fragment linked to a therapeutic agent. In some embodiments, the therapeutic agent is a cytotoxic agent. The cytotoxic agent can be selected from a group consisting of ricin, ricin A-chain, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin mitogellin, retstrictocin, phenomycin, enomycin, curicin, crotin, calicheamicin, *Sapaonaria officinalis* inhibitor, maytansinoids, and glucocorticoidricin. The therapeutic agent can be a radioactive isotope. The therapeutic isotope can be selected from the group consisting of $^{212}Bi$, $^{131}I$, $^{111}In$, $^{90}Y$ and $^{186}Re$.

In any of the embodiments above, a chemotherapeutic drug and/or radiation therapy can be administered further. In some embodiments, the patient also receives hormone antagonist therapy. The contacting of the patient with the antibody or antibody fragment, can be by administering the antibody to the patient intravenously, intraperitoneally, intramuscularly, intratumorally, or intradermally.

In some embodiments, the immunoconjugate includes a cytotoxic agent which is a small molecule. Toxins such as maytansin, maytansinoids, saporin, gelonin, ricin or calicheamicin and analogs or derivatives thereof are also suitable. Other cytotoxic agents that can be conjugated to the anti-EMP2 antibodies include BCNU, streptozoicin, vincristine and 5-fluorouracil. Enzymatically active toxins and fragments thereof can also be used. The radio-effector moieties may be incorporated in the conjugate in known ways (e.g., bifunctional linkers, fusion proteins). The antibodies of the present invention may also be conjugated to an effector moiety which is an enzyme which converts a prodrug to an active chemotherapeutic agent. See, WO 88/07378; U.S. Pat. Nos. 4,975,278; and 6,949,245. The antibody or immunoconjugate may optionally be linked to nonprotein polymers (e. g., polyethylene glycol, polypropylene glycol, polyoxyalkylenes, or copolymers of polyethylene glycol and polypropylene glycol).

Conjugates of the antibody and cytotoxic agent may be made using methods well known in the art (see, U.S. Pat. No. 6,949,245). For instance, the conjugates may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52: 127-131 (1992)) may be used.

In other embodiments, the methods provided herein are implemented in conjunction with other cancer therapies (e.g., radical prostatectomy), radiation therapy (external beam or brachytherapy), hormone therapy or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly.

Antibody Compositions for In Vivo Administration

Formulations of the subject anti-EMP2 antibodies provided herein are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunoconjugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as SFU, vinblastine, actinomycin D, cisplatin, methotrexate, and the like.

The combined administrations contemplates coadministration, using separate formulations or a single pharmaceutical formulation, and consecutive administration in either order, wherein preferably there is a time period while both (or all) active agents simultaneously exert their biological activities.

Molecules and compounds identified that indirectly or directly modulate the expression and/or function of a EMP2 can be useful in treating cancers that, respectively, overexpress EMP2. Thesen modulators can be administered alone or co-administered in combination with conventional chemotherapy, radiotherapy or immunotherapy as well as currently developed therapeutics.

The formulation herein may also contain more than one active compound as necessary for the particular indication being treated, preferably those with complementary activities that do not adversely affect each other. For example, it may be desirable to provide antibodies with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administrative Modalities

The antibodies and chemotherapeutic agents of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain aspects, the antibodies and chemotherapeutic agents of the invention are administered to a subject with cancer. In certain aspects, the antibodies and chemotherapeutic agents of the invention are administered to a subject with breast cancer. In certain aspects, the antibodies and chemotherapeutic agents of the invention are administered to a subject with triple negative breast cancer. Intravenous or subcutaneous administration of the antibody is preferred.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling.

In addition to these positive therapeutic responses, the subject undergoing therapy may experience the beneficial effect of an improvement in the symptoms associated with the disease.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-EMP2 antibodies used in the present invention depend on the disease or condition to be treated and may be determined by the persons skilled in the art.

An exemplary, non-limiting range for a therapeutically effective amount of an anti-EMP2 antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, the antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the anti-EMP2 antibody is administered by infusion in a weekly dosage of from 10 to 500 mg/kg such as from 200 to 400 mg/kg. Such administration may be repeated, e.g., 1 to 8 times, such as 3 to 5 times. The administration may be performed by continuous infusion over a period of from 2 to 24 hours, such as from 2 to 12 hours.

In one embodiment, the anti-EMP2 antibody is administered by slow continuous infusion over a long period, such as more than 24 hours, if required to reduce side effects including toxicity.

In one embodiment the anti-EMP2 antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-EMP2 antibody.

In a further embodiment, the anti-EMP2 antibody is administered once weekly for 2 to 12 weeks, such as for 3 to 10 weeks, such as for 4 to 8 weeks.

In one embodiment, the anti-EMP2 antibody is administered by maintenance therapy, such as, e.g., once a week for a period of 6 months or more.

In one embodiment, the anti-EMP2 antibody is administered by a regimen including one infusion of an anti-EMP2 antibody followed by an infusion of an anti-EMP2 antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Combination Therapy

In some embodiments the anti-EMP2 antibody molecule thereof is used in combination with one or more additional therapeutic agents, e.g. a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and other inhibitors of proteins or enzymes known to be upregulated, over-expressed or activated in cancers, the inhibition of which downregulates cell replication.

In some embodiments, the antibodies of the invention can be used prior to, concurrent with, or after treatment with any of the chemotherapeutic agents described herein or known to the skilled artisan at this time or subsequently.

Efficacy of Methods Described Herein

In certain aspects of this invention, efficacy of anti-EMP2 therapy is measured by decreased serum concentrations of tumor specific markers, increased overall survival time, decreased tumor size, cancer remission, decreased metastasis marker response, and decreased chemotherapy adverse affects.

In certain aspects of this invention, efficacy is measured with companion diagnostic methods and products. Companion diagnostic measurements can be made before, during, or after anti-EMP2 treatment.

Companion Diagnostics

In one embodiment of the invention's second aspect, a diagnostic or prognostic assay will be performed to determine whether the patient's cancer is characterized by overexpression of EMP2. Various assays for determining such amplification/overexpression are contemplated and include the immunohistochemistry, FISH and shed antigen assays, southern blotting, or PCR techniques. Moreover, the EMP2 overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label. In some embodiments, the cancer to be treated is not yet invasive, but overexpresses EMP2.

In other embodiments, this disclosure relates to companion diagnostic methods and products. In one embodiment, the companion diagnostic method and products can be used to monitor the treatment of breast cancer, specifically triple negative breast cancer, as described herein. In some embodiments, the companion diagnostic methods and products include molecular assays to measure levels of proteins, genes or specific genetic mutations. Such measurements can be used, for example, to predict whether anti-EMP2 therapy will benefit a specific individual, to predict the effective dosage of anti-EMP2 therapy, to monitor anti-EMP2 therapy, adjust anti-EMP2 therapy, tailor the anti-EMP2 therapy to an individual, and track cancer progression and remission.

In some embodiments, the companion diagnostic can be used to monitor a combination therapy.

In some embodiments, the companion diagnostic can include an anti-EMP2 antibody described herein.

In some embodiments, the companion diagnostic can be used before, during, or after anti-EMP2 therapy.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

EXAMPLES

Example 1: Construction of Subject Anti-EMP2 Antibodies

Figure 12:
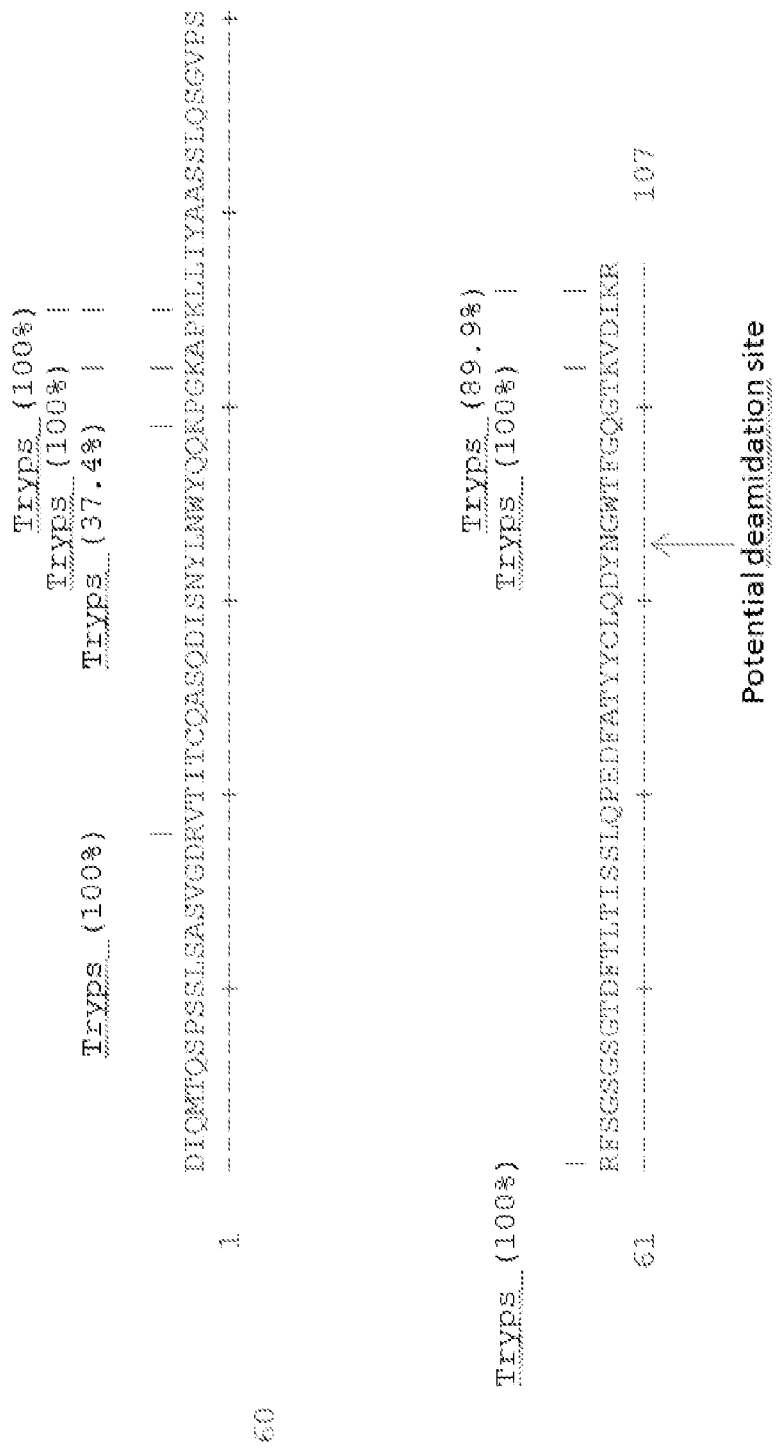
FIG. 12 shows a computer algorithm prediction of deamidation sites in the variable light chain CDR3 of PG-101.

A computer algorithm predicted a potential deamidation site in the light chain CDR3 of PG-101. (FIG. 12). In order to confirm the sequence liability, PG-101 was cleaved using trypsin and then subjected to mass-spectometry. Mass spec confirmed that the predicted site in the variable light chain CDR3 was susceptibility to cleavage. (FIG. 13)

Two variants (referred to as "Variant 1" and "Variant 2") of anti-EMP2 antibody PG-101 (referred to as PG-101 parental) were constructed to eliminate the deamidation site in the variable light chain CDR3 of PG-101

The PG-101 Parental, PG-101 Variant 1 and PG-101 Variant 2 antibodies were cloned into a high expression mammalian vector system and three small-scale (0.03 liter) premium transient production runs were completed in HEK293 cells. The antibodies were purified by Protein A purification and 4.58 mg of PG-101 Parental, 3.18 mg of PG-101 Variant 1 and 5.10 mg of PG-101 Variant 2 were obtained.

The amino acid sequence of the heavy and light chain of PG-101 Parental, PG-101 Variant 1 and PG-101 Variant 2 antibodies are shown below, with the variable region of each shaded in grey:

PG-101 Parental HC-hIgG1:
(SEQ ID NO: 17)
MDPKGSLSWRILLFLSLAFELSYGQVQLVQSGGGVVQPGRSLRLSCAA

SGFTFSSYAMHWVRQAPGKGLEWVAVISYDGSNKYYADSVKGRFTISR

DNSKNTLYLQMNSLRAEDTAVYYCARDRRGRKSAGIDYWGQGTLVTVS

SASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSF

FLYSKLTVDKSRWQQGNVFSCSVMHEALHNHYTQKSLSLSPG

PG-101 Parental LC-hKappa:
(SEQ ID NO: 18)
METDTLLLWVLLLWVPGSTGDIQMTQSPSSLSASVGDRVTITCQASQD

ISNYLNWYQQKPGKAPKLLIYAASSLQSGVPSRFSGSGSGTDFTLTIS

SLQPEDFATYYCLQDYNGWTFGQGTKVDIKRTVAAPSVFIFPPSDEQL

KSGTASVVCLLNNFYPREAKVQWKVDNALQSGNSQESVTEQDSKDSTY

SLSSTLTLSKADYEKHKVYACEVTHQGLSSPVTKSFNRGEC

PG-101 LC Variant 1-hKappa:
(SEQ ID NO: 19)
METDTLLLWVLLLWVPGSTGDIQMTQSPSSLSASVGDRVTITCQASQD

ISNYLNWYQQKPGKAPKLLIYAASSLQSGVPSRFSGSGSGTDFTLTIS

SLQPEDFATYYCLQDYSGWTFGQGTKVDIKRTVAAPSVFIFPPSDEQL

KSGTASVVCLLNNFYPREAKVQWKVDNALQSGNSQESVTEQDSKDSTY

SLSSTLTLSKADYEKHKVYACEVTHQGLSSPVTKSFNRGEC

PG-101 LC Variant 2-hKappa:
(SEQ ID NO: 20)
METDTLLLWVLLLWVPGSTGDIQMTQSPSSLSASVGDRVTITCQASQD

ISNYLNWYQQKPGKAPKLLIYAASSLQSGVPSRFSGSGSGTDFTLTIS

SLQPEDFATYYCLQDYNLWTFGQGTKVDIKRTVAAPSVFIFPPSDEQL

KSGTASVVCLLNNFYPREAKVQWKVDNALQSGNSQESVTEQDSKDSTY

SLSSTLTLSKADYEKHKVYACEVTHQGLSSPVTKSFNRGEC

The nucleotide sequence of each heavy and light chain are depicted below:

PG-101 Parental HC-hIgG1:
(SEQ ID NO: 21)
ATGGACCCCAAGGGCAGCCTGAGCTGGAGAATCCTGCTGTTCCTGAGCCT

GGCCTTCGAGCTGAGCTACGGCCAGGTGCAGCTGGTGCAGTCTGGCGGCG

GAGTGGTGCAGCCTGGAAGATCCCTGAGACTGTCCTGTGCCGCCTCCGGC

TTCACCTTCTCCAGCTACGCTATGCACTGGGTGCGACAGGCCCCTGGCAA

GGGACTGGAATGGGTGGCCGTGATCTCCTACGACGGCTCCAACAAGTACT

ACGCCGACTCCGTGAAGGGCCGGTTCACCATCTCCCGGGACAACTCCAAG

AACACCCTGTACCTGCAGATGAACTCCCTGCGGGCCGAGGACACCGCCGT

GTACTACTGCGCCAGAGACAGACGGGGCAGAAAGTCCGCCGGCATCGATT

ATTGGGGCCAGGGCACCCTCGTGACCGTGTCCTCTGCTAGCACCAAGGGC

CCCAGCGTGTTCCCTCTGGCCCCCAGCAGCAAGAGCACCAGCGGCGGAAC

CGCCGCCCTGGGCTGCCTGGTGAAGGACTACTTCCCCGAGCCCGTGACCG

TGTCCTGGAACAGCGGCGCTCTGACCAGCGGAGTGCACACCTTCCCTGCC

GTGCTGCAGAGCAGCGGCCTGTACTCCCTGAGCAGCGTGGTGACCGTGCC

CAGCAGCAGCCTGGGCACCCAGACCTACATCTGCAACGTGAACCACAAGC

CCTCCAACACCAAGGTGGACAAGAAGGTGGAGCCTAAGAGCTGCGACAAG

ACCCACACCTGCCCTCCCTGCCCCGCCCCCGAGCTGCTGGGCGGACCCAG

CGTGTTCCTGTTCCCTCCCAAGCCCAAGGACACCCTGATGATCAGCCGCA

CCCCCGAGGTGACCTGCGTGGTGGTGGACGTGAGCCACGAGGACCCCGAG

GTGAAGTTCAACTGGTACGTGGACGGCGTGGAGGTGCACAACGCCAAGAC

CAAGCCTCGGGAGGAGCAGTACAACTCCACCTACCGCGTGGTGAGCGTGC

TGACCGTGCTGCACCAGGACTGGCTGAACGGCAAGGAGTACAAGTGCAAG

GTGAGCAACAAGGCCCTGCCCGCTCCCATCGAGAAGACCATCAGCAAGGC

CAAGGGCCAGCCCCGGGAGCCTCAGGTGTACACCCTGCCCCCCAGCCGCG

ACGAGCTGACCAAGAACCAGGTGAGCCTGACCTGCCTGGTGAAGGGCTTC

TACCCCTCCGACATCGCCGTGGAGTGGGAGAGCAACGGCCAGCCTGAGAA

CAACTACAAGACCACCCCTCCCGTGCTGGACAGCGACGGCAGCTTCTTCC

TGTACAGCAAGCTGACCGTGGACAAGTCCCGGTGGCAGCAGGGCAACGTG

TTCAGCTGCAGCGTGATGCACGAGGCCCTGCACAACCACTACACCCAGAA

GAGCCTGAGCCTGAGCCCCGGATAG

PG-101 Parental LC-hKappa:
(SEQ ID NO: 22)
ATGGAGACCGACACCCTGCTGCTCTGGGTGCTGCTGCTCTGGGTGCCCGG

CTCCACCGGAGACATCCAGATGACCCAGTCCCCCTCCAGCCTGTCTGCCT

CTGTGGGCGACAGAGTGACCATCACCTGTCAGGCCTCCCAGGACATCTCC

AACTACCTGAACTGGTATCAGCAGAAGCCCGGCAAGGCCCCCAAGCTGCT

GATCTACGCTGCCAGCTCTCTGCAGTCCGGCGTGCCCTCTAGATTCTCCG

GCTCTGGCTCTGGCACCGACTTTACCCTGACCATCAGCTCCCTGCAGCCC

GAGGACTTCGCCACCTACTACTGTCTGCAAGACTACAACGGCTGGACCTT

CGGCCAGGGCACCAAGGTGGACATCAAGCGGACCGTGGCCGCCCCCAGCG

-continued

TGTTCATCTTCCCTCCCAGCGACGAGCAGCTGAAGTCTGGCACCGCCAGC

GTGGTGTGCCTGCTGAACAACTTCTACCCCCGCGAGGCCAAGGTGCAGTG

GAAGGTGGACAACGCCCTGCAGAGCGGCAACAGCCAGGAGAGCGTGACCG

AGCAGGACTCCAAGGACAGCACCTACAGCCTGAGCAGCACCCTGACCCTG

AGCAAGGCCGACTACGAGAAGCACAAGGTGTACGCCTGCGAGGTGACCCA

CCAGGGACTGTCTAGCCCCGTGACCAAGAGCTTCAACCGGGGCGAGTGCT

AA

PG-101 LC Variant 1-hKappa:
(SEQ ID NO: 23)
ATGGAGACCGACACCCTGCTGCTCTGGGTGCTGCTGCTCTGGGTGCCCGG

CTCCACCGGAGACATCCAGATGACCCAGTCCCCCTCCAGCCTGTCTGCCT

CTGTGGGCGACAGAGTGACCATCACCTGTCAGGCCTCCCAGGACATCTCC

AACTACCTGAACTGGTATCAGCAGAAGCCCGGCAAGGCCCCCAAGCTGCT

GATCTACGCTGCCAGCTCTCTGCAGTCCGGCGTGCCCTCTAGATTCTCCG

GCTCTGGCTCTGGCACCGACTTTACCCTGACCATCAGCTCCCTGCAGCCC

GAGGACTTCGCCACCTACTACTGTCTGCAAGACTACAGCGGCTGGACCTT

CGGCCAGGGCACCAAGGTGGACATCAAGCGGACCGTGGCCGCCCCCAGCG

TGTTCATCTTCCCTCCCAGCGACGAGCAGCTGAAGTCTGGCACCGCCAGC

GTGGTGTGCCTGCTGAACAACTTCTACCCCCGCGAGGCCAAGGTGCAGTG

GAAGGTGGACAACGCCCTGCAGAGCGGCAACAGCCAGGAGAGCGTGACCG

AGCAGGACTCCAAGGACAGCACCTACAGCCTGAGCAGCACCCTGACCCTG

AGCAAGGCCGACTACGAGAAGCACAAGGTGTACGCCTGCGAGGTGACCCA

CCAGGGACTGTCTAGCCCCGTGACCAAGAGCTTCAACCGGGGCGAGTGCT

AA

PG-101 LC Variant 2-hKappa:
(SEQ ID NO: 24)
ATGGAGACCGACACCCTGCTGCTCTGGGTGCTGCTGCTCTGGGTGCCCGG

CTCCACCGGAGACATCCAGATGACCCAGTCCCCCTCCAGCCTGTCTGCCT

CTGTGGGCGACAGAGTGACCATCACCTGTCAGGCCTCCCAGGACATCTCC

AACTACCTGAACTGGTATCAGCAGAAGCCCGGCAAGGCCCCCAAGCTGCT

GATCTACGCTGCCAGCTCTCTGCAGTCCGGCGTGCCCTCTAGATTCTCCG

GCTCTGGCTCTGGCACCGACTTTACCCTGACCATCAGCTCCCTGCAGCCC

GAGGACTTCGCCACCTACTACTGTCTGCAAGACTACAACCTGTGGACCTT

CGGCCAGGGCACCAAGGTGGACATCAAGCGGACCGTGGCCGCCCCCAGCG

TGTTCATCTTCCCTCCCAGCGACGAGCAGCTGAAGTCTGGCACCGCCAGC

GTGGTGTGCCTGCTGAACAACTTCTACCCCCGCGAGGCCAAGGTGCAGTG

GAAGGTGGACAACGCCCTGCAGAGCGGCAACAGCCAGGAGAGCGTGACCG

AGCAGGACTCCAAGGACAGCACCTACAGCCTGAGCAGCACCCTGACCCTG

AGCAAGGCCGACTACGAGAAGCACAAGGTGTACGCCTGCGAGGTGACCCA

CCAGGGACTGTCTAGCCCCGTGACCAAGAGCTTCAACCGGGGCGAGTGCT

AA

Example 2: Binding Characteristics of PG-101 Antibody and Variants

Figure 2:
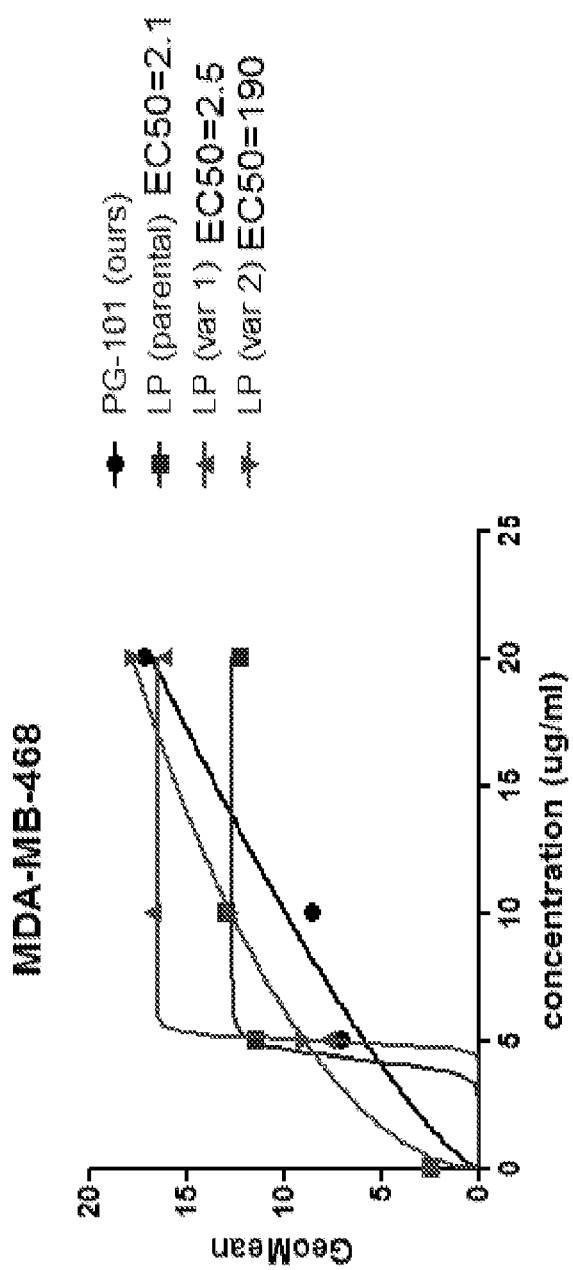
FIG. 2 includes graphs, showing PG-101 and variant binding to MDA-MB-468 cells. PG-101 (prior to formulation) was compared with reformulated PG-101, variant 1 and Variant 2.

The binding characteristics of PG-101 antibody and variants were tested. First, the titration of anti-EMP2 IgG1 antibodies on SUM149 cells were tested using flow cytometery (FIG. 1, left) The KD was determined at 2.6 using nonlinear regression analysis. To confirm the specificity and sensitivity of binding, rituximab was utilized as a negative control (FIG. 1, right). Next, PG-101 and variant binding to MDA-MB-468 cells were tested (FIG. 2). PG-101 (prior to formulation) was compared with reformulated PG-101, Variant 1 and variant 2. Variant 2 did not reach saturation, and buffer reformation improved the binding affinity of the parental antibody to EMP2.

Figure 3:
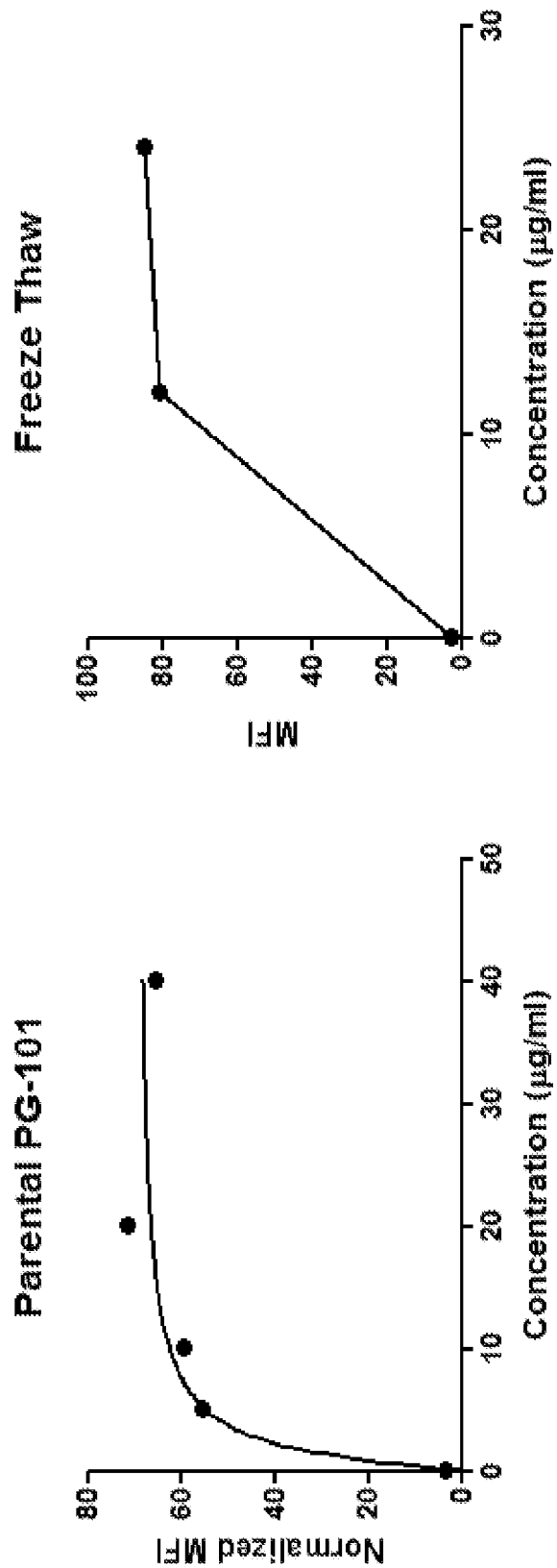
FIG. 3 includes graphs, depicting experiments designed to test the stability of the reformulation of PG-101. Left is a graph measuring the binding affinity of PG-101 on SUM149 cells using flow cytometry. Right is a graph showing the binding of PG-101 after freezing and thawing.

Stability of reformulated PG-101 was also tested. (FIG. 3). Specifically, the binding affinity of reformulated PG-101 on SUM149 cells were tested using flow cytometry (FIG. 3, left). The KD was determined at 2.6 using nonlinear regression analysis. In addition, binding of PG-101 on SUM149 cells after freezing and thawing was tested. As shown in FIG. 3, no differences between freshly prepared antibody (on the left) and the freeze-thawed sample (on the right) were observed.

Figure 4:
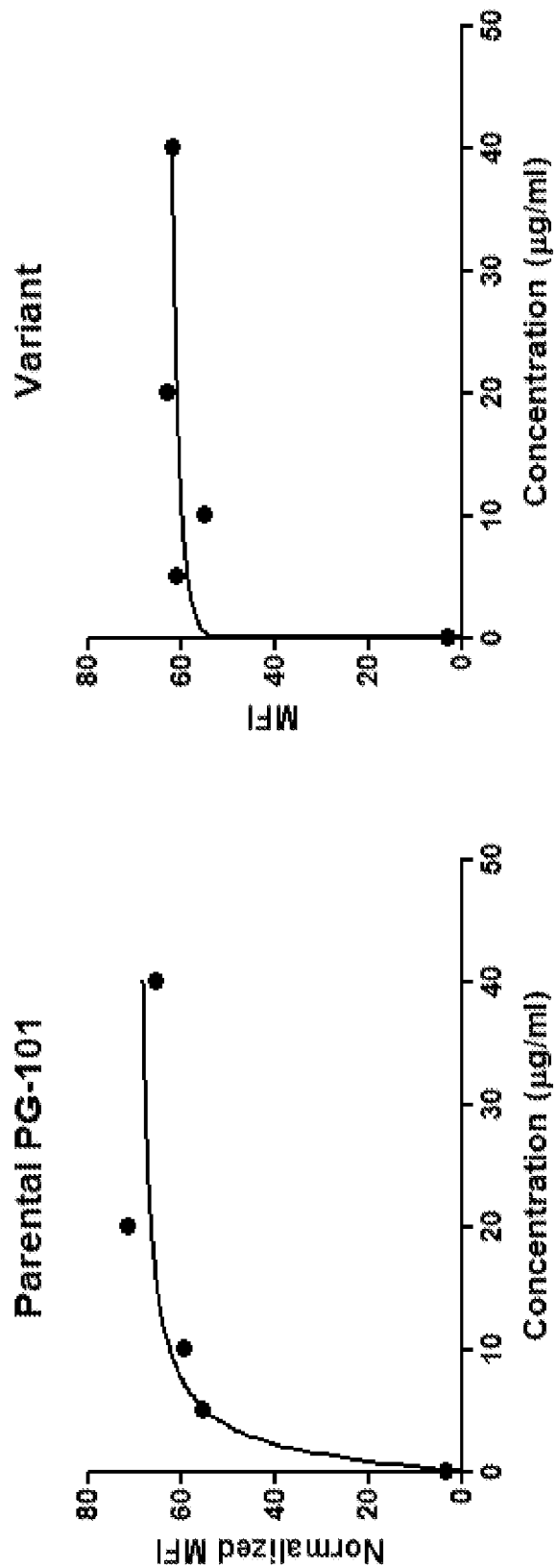
FIG. 4 includes graphs, showing that anti-EMP2 variant 1 retains binding to EMP2 with improved affinity. PG-101 and variant 1 binding to EMP2 was determined using SUM149 and flow cytometry.

A comparison of anti-EMP2 Variant 1 and PG-101 binding affinity for EMP2 was carried out. As shown in FIG. 4, anti-EMP2 Variant 1 retains binding to EMP2 with improved affinity. PG-101 and Variant 1 binding to EMP2 was determined using SUM149 and flow cytometry. Variant 1 retains binding to EMP2 with improved affinity. Flow cytometry was used to determine the ability of both antibodies to bind to EMP2 on SUM149 cells. The KD for the parental antibody was 2.6 µg/ml nonlinear regression analysis while there was greater than a two fold increase in binding with Variant 1.

Figure 6:
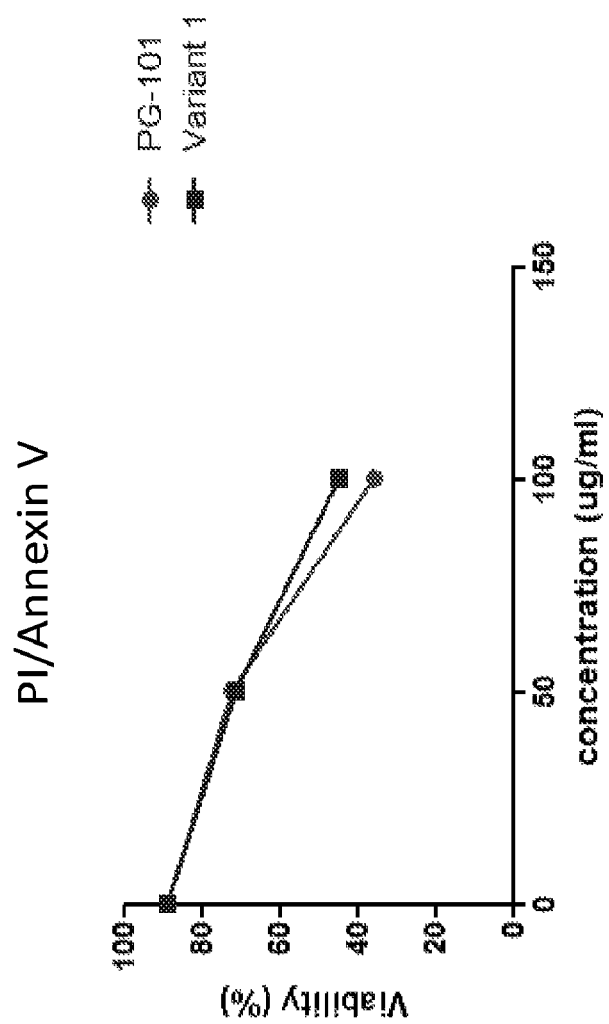
FIG. 6 is a graph, showing the ability of the PG-101 vs. Variant 1 to induce cell death in a second independent experiment. Cell death was measured by quantitating annexin V/propidium iodide staining using flow cytometry.
Figure 7:
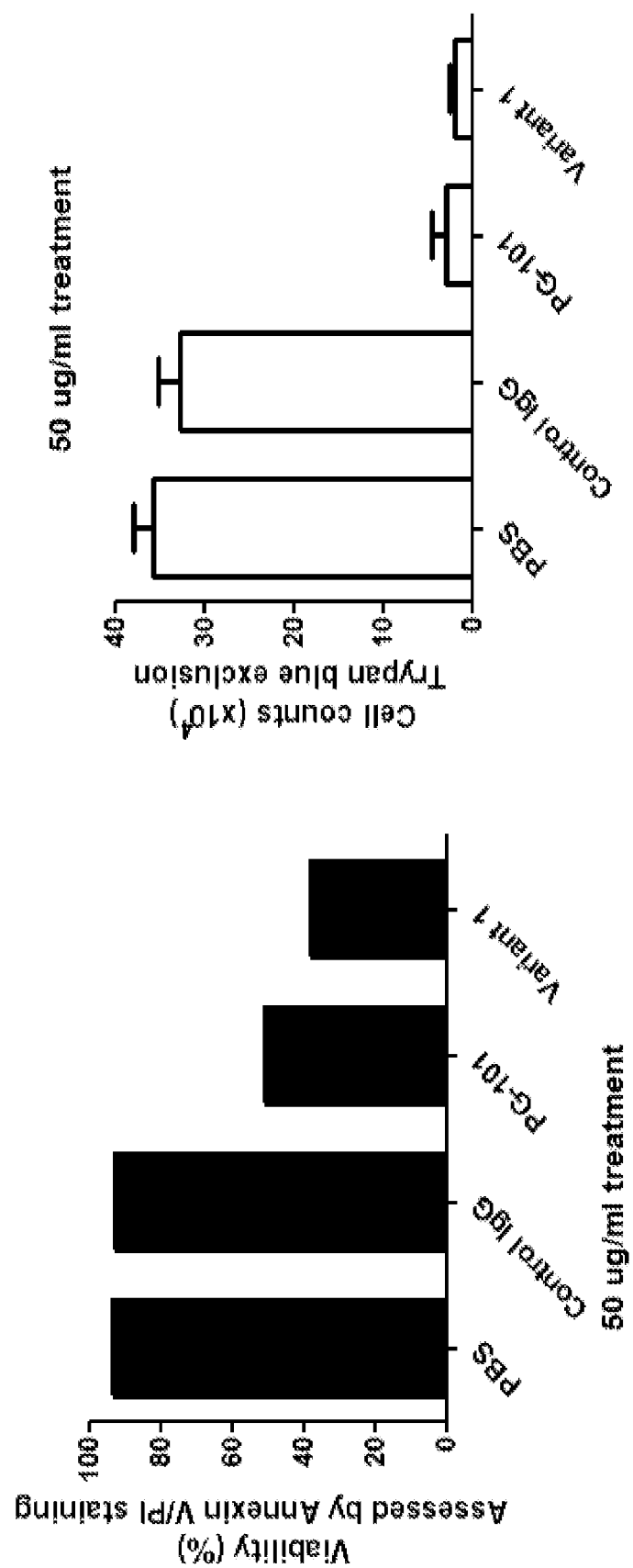
FIG. 7 are graphs, showing the ability of PG-101 vs. variant 1 to induce cell death in MDA-MB-468 cells, in a third independent experiment. Left, cell death was determined by quantitating annexin V/propidium iodide staining using flow cytometry. Cells were incubated with 50 µg/ml control IgG, PG-101, or variant 1 for 5 days. Right, cell numbers were enumerated using trypan blue exclusion.

Example 3: Functional Activity of PG-101 vs. Variant Anti-EMP2 Antibodies In Vitro The ability of PG-101 and Variant 1 to induce cell death was determined in three independent experiments (FIGS. 5-7). Briefly, MDA-MB-468 cells were incubated with varying concentrations of anti-EMP2 antibodies for 5 days. Cell death was measured by quantitating annexin V/propidium iodide staining using flow cytometry (FIG. 5, left). Total cell numbers following incubation for 5 days were enumerated using trypan blue exclusion (FIG. 5, right). The two independent experiments in FIGS. 5 and 6 were carried out using varying concentrations of anti-EMP2 antibodies and control whereas the experiment in FIG. 7 was carried out using 50 µg/ml of antibodies and control for 5 days. As shown in these figures, PG-101 and Variant 1 were both able to induce cell death.

Figure 9:
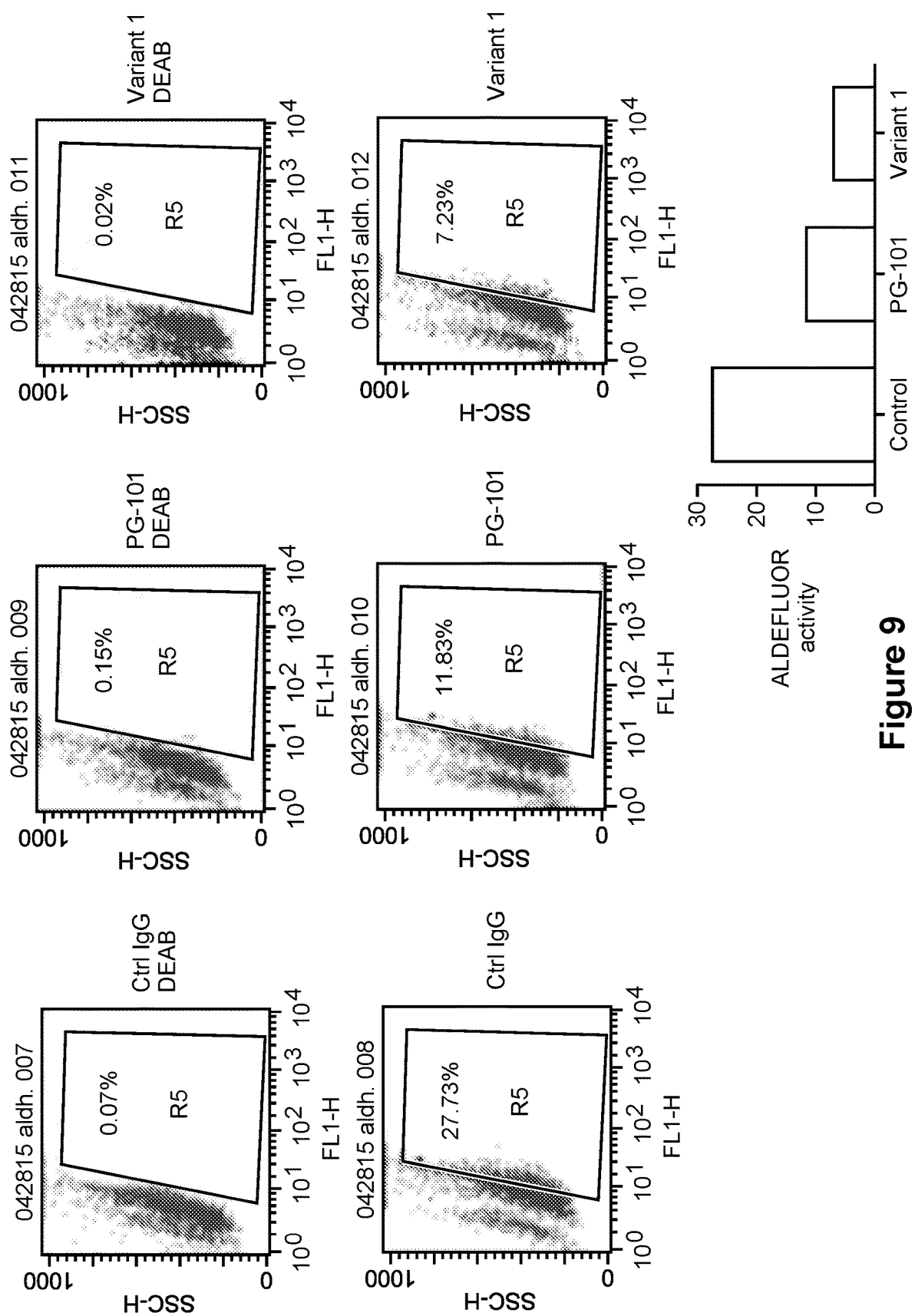
FIG. 9. Depict a third independent study showing the subject anti-EMP2 antibodies ability to reduce ALDH activity in MDA-MB-468. The flow cytometry raw results are presented on the left and shown graphically on the right.

To determine the ability of the subject anti-EMP2 antibodies to inhibit cancer stem cells, MDA-MB-468 cells were incubated with varying concentrations of PG-101 and variant 1 and ALDH activity was assessed in three independent experiments (FIGS. 8 and 9). In FIG. 8, MDA-MB-468 cells were incubated with varying concentrations of PG-101 and Variant 1. Both reagents significantly reduced ALDH activity, a measure of cancer stem cells. In FIG. 9, treatment of MDA-MB-468 cells for 24 hours showed a reduction in ALDH activity. The flow cytometry raw results are presented on the left and shown graphically on the right.

Figure 10:
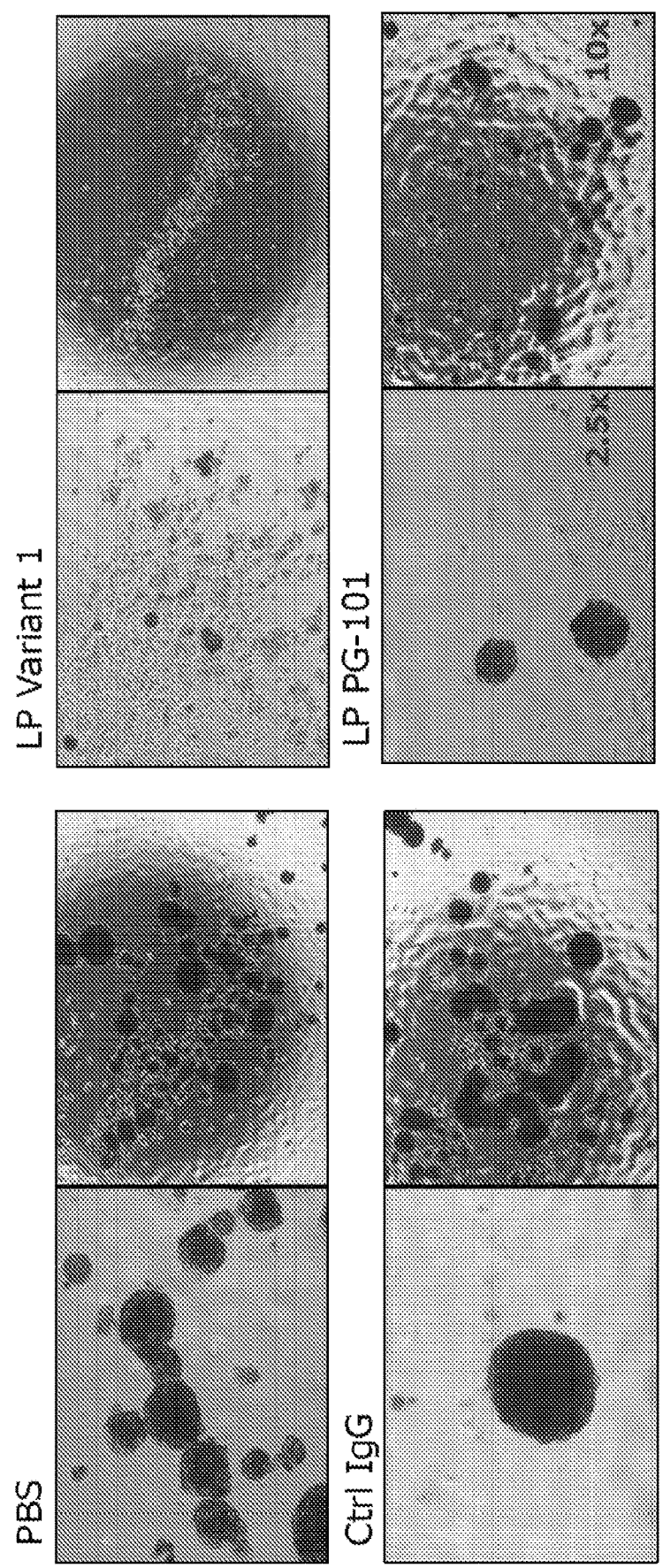
FIGS. 10 and 11 shows the ability of the subject anti-EMP2 antibodies to inhibit cancer stem cells using a mammosphere formation assay.
Figure 11:
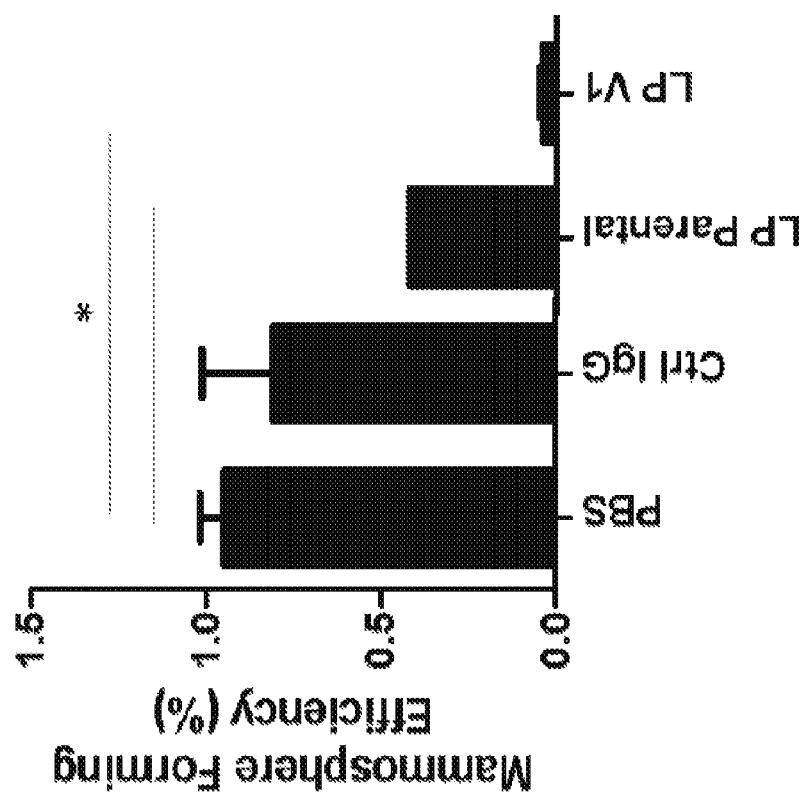

The ability of the subject anti-EMP2 antibodies to inhibit cancer stem cells were also assessed using a mammosphere formation assay (FIGS. 10 and 11). Mammosphere formation is another hallmark of cancer stem cells. Briefly, control IgG, PG-101, or variant 1 were incubated for 2 weeks with BT474 cells. FIG. 10 shows raw images of the cells post incubation. FIG. 11 shows enumeration of mammospheres in triplicate wells. *, $p<0.05$ using Student's t test. As shown in the these studies, both PG-101 and Variant 1 were able to reduce mammosphere formation, with Variant 1 being able to reduce mammosphere formation more than PG-101.

Figure 14:
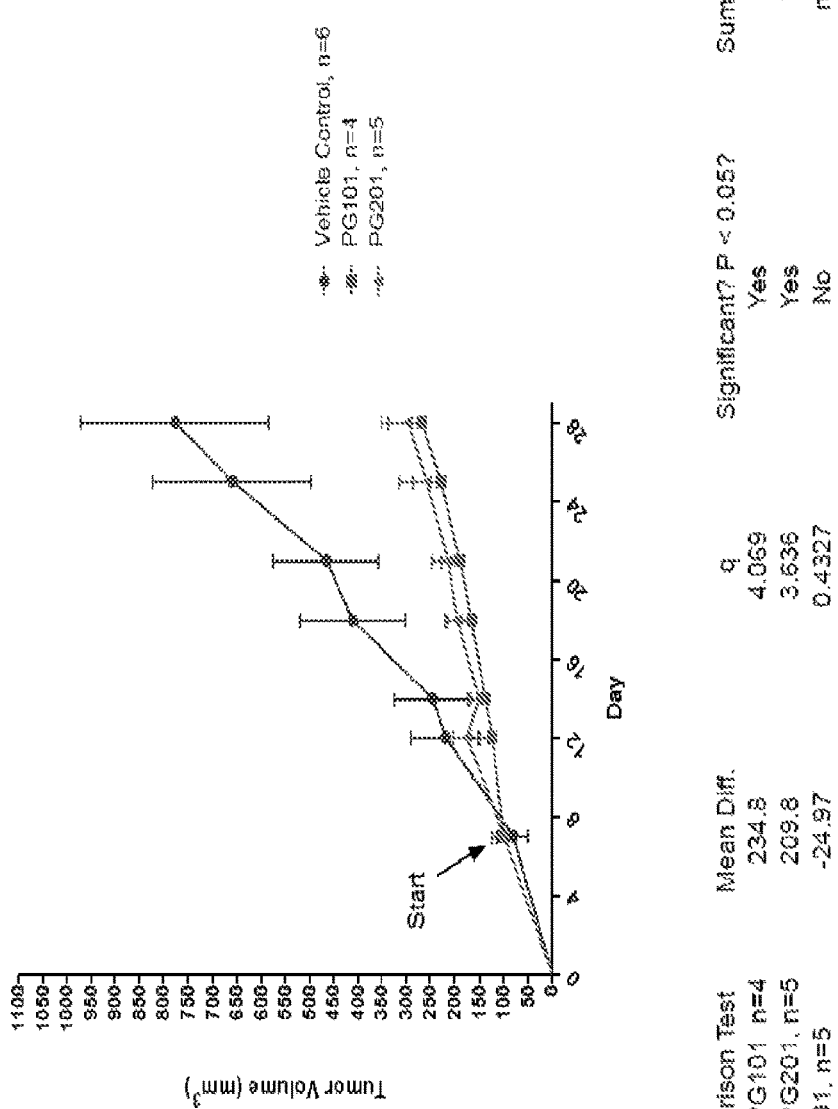
FIG. 14 provides a summary of the ability of PG101 and Variant 1 (now termed "PG-201") to reduce tumor load in vivo in an endometrial cancer model.
Figure 15:
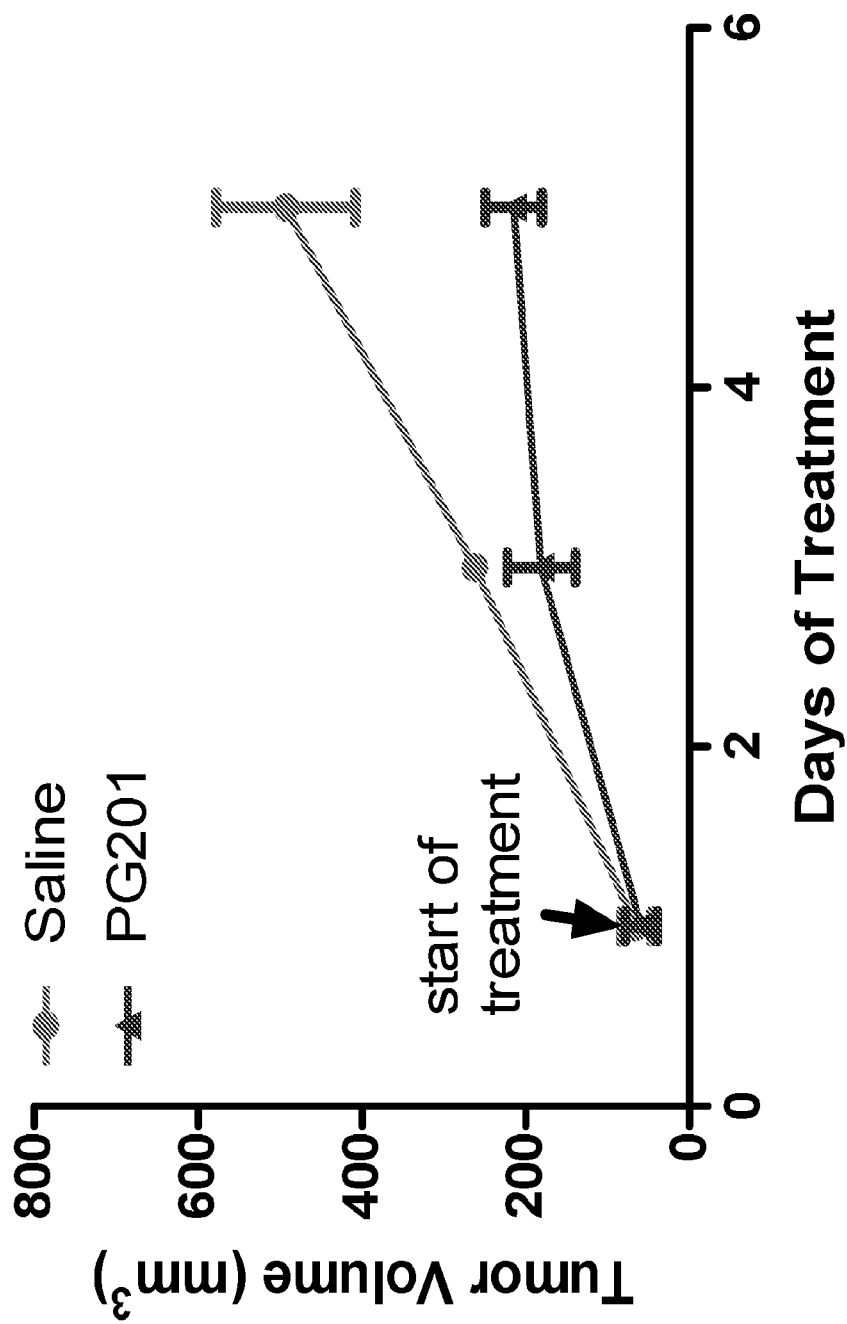
FIG. 15 provides a summary of the ability of Variant 1 ("PG-201") to reduce tumor load in vivo in a breast cancer cell model.

Example 4: Functional Activity of PG-101 vs. Variant Anti-EMP2 Antibodies In Vivo The ability of PG101 and variant 1 (now termed PG-201) to reduce tumor load in vivo was determined (FIGS. 14 and 15). Briefly, HEC1a endometiral cancer xenografts were created in Balb/c nude animals. When tumors approached 100 mm3, they were treated with 10 mg/kg IP twice a week with a vehicle control, PG-101 or PG-201. As shown in FIG. 14, both PG-101 and PG-201 reduced tumor load significantly.

As shown in FIG. 15, PG-201 also effectively reduced tumor load in a murine model of breast cancer. 4T1 cells were implanted into the mammary fat pad of Balb/c mice. Mice were treated twice a week with 10 mg/kg of PG-201 or saline. As shown in FIG. 13, PG201 reduced tumor load as compared to a saline control.

Example 5: PG-201 are Useful as Antibody Drug Conjugates

Figure 16:
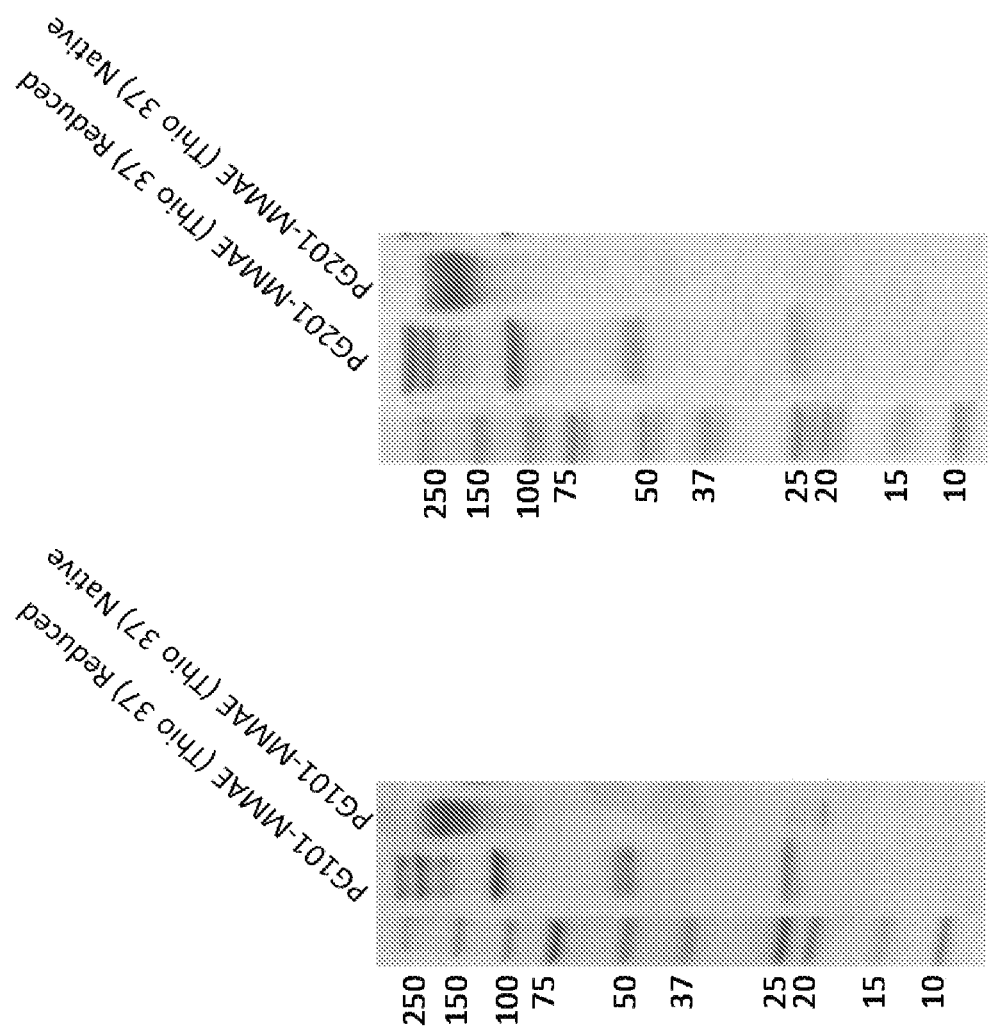
FIG. 16 shows that the CDR3 deamination site in PG-101 prevents its use as an antibody drug conjugate.

To assess whether PG-101 and PG-201 could be used as drug conjugates, PG-101 and PG-201 was reduced to expose the interchain disulfide bonds and then rebridged using a thiolinker (FIG. 16). The thiolinker was then attached to DBCO-MMAE (monomethyl auristatin E) using click chemistry to generate an antibody drug conjugate. Successful rebridged antibodies show only a ~160 kD (native)(PG-201, FIG. 16, right). PG-101 consistently showed light chain fragments in the native antibody (FIG. 16, left), suggesting a lack of stability of the antibody drug conjugate.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An isolated antibody that binds to Epithelial Membrane Protein 2 (EMP2), comprising a heavy chain variable region and a light chain variable region, wherein the heavy chain variable region comprises three heavy chain complementary determining regions (HCDRs) and wherein the light chain variable region comprises three light chain variable regions (LCDRs), wherein: the sequence of HCDR1 is SEQ ID NO:11, the sequence of HCDR2 is SEQ ID NO:12, the sequence of HCDR3 is SEQ ID NO:13, the sequence of LCDR1 is SEQ ID NO:14, the sequence of LCDR2 is SEQ ID NO:15, and the sequence of LCDR3 is SEQ ID NO:16.

2. The antibody of claim 1, wherein the antibody comprises the heavy chain variable region comprising the amino acid sequence according to SEQ ID NO:3 and the light chain variable region comprising the amino acid sequence according to SEQ ID NO:4.

3. The antibody of claim 2, wherein the antibody comprises a heavy chain comprising the amino acid sequence according to SEQ ID NO:6 and a light chain comprising the amino acid sequence to SEQ ID NO:7.

4. The antibody of claim 1, wherein the antibody is an scFv, a diabody, minibody, or triabody, a chimeric antibody, or a recombinant antibody.

5. The antibody of claim 1, wherein the antibody is conjugated to a cytotoxic agent or a label.

6. A pharmaceutical composition comprising the antibodies of claim 1 and a physiologically acceptable carrier.

7. A method of treating or reducing the rate of reoccurrence of an EMP2 expressing cancer in a patient, the method comprising:
administering to the patient an effective amount of an anti-EMP2 antibody comprising a heavy chain variable region and a light chain variable region, wherein the heavy chain variable region comprises three heavy chain complementary determining regions (HCDRs) and wherein the light chain variable region comprises three light chain variable regions (LCDRs), wherein: the sequence of HCDR1 is SEQ ID NO:11, the sequence of HCDR2 is SEQ ID NO:12, the sequence of HCDR3 is SEQ ID NO:13, the sequence of LCDR1 is SEQ ID NO:14, the sequence of LCDR2 is SEQ ID NO:15, and the sequence of LCDR3 is SEQ ID NO:16.

8. The method of claim 7, wherein the antibody comprises the heavy chain variable region comprising the amino acid sequence according to SEQ ID NO:3 and the light chain variable region comprising the amino acid sequence according to SEQ ID NO:4.

* * * * *